United States Patent
Goto et al.

(10) Patent No.: US 9,642,588 B2
(45) Date of Patent: May 9, 2017

(54) X-RAY COMPUTER TOMOGRAPHIC APPARATUS AND SCAN PLAN SETTING SUPPORTING APPARATUS

(71) Applicant: Toshiba Medical Systems Corporation, Otawara-shi (JP)

(72) Inventors: Takahiro Goto, Nasushiobara (JP); Shinsuke Tsukagoshi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 216 days.

(21) Appl. No.: 14/692,059

(22) Filed: Apr. 21, 2015

(65) Prior Publication Data
US 2015/0297166 A1    Oct. 22, 2015

(30) Foreign Application Priority Data
Apr. 21, 2014 (JP) ................. 2014-087762

(51) Int. Cl.
*A61B 6/03* (2006.01)
*A61B 6/00* (2006.01)
(Continued)

(52) U.S. Cl.
CPC .............. *A61B 6/542* (2013.01); *A61B 6/032* (2013.01); *A61B 6/06* (2013.01); *A61B 6/4035* (2013.01);
(Continued)

(58) Field of Classification Search
CPC ........... A61B 5/032; A61B 5/06; A61B 5/463; A61B 5/465; A61B 5/466; A61B 5/469;
(Continued)

(56) References Cited

U.S. PATENT DOCUMENTS

2004/0190674 A1* 9/2004 Tsukagoshi ............ A61B 6/032
378/4
2008/0037714 A1* 2/2008 Sakaida ................. A61B 6/032
378/207
(Continued)

FOREIGN PATENT DOCUMENTS

JP            07-023946       1/1995
JP        2004-298247 A      10/2004
(Continued)

OTHER PUBLICATIONS

"SmartExam", Magnetic resonance, Royal Philips Electronics N.V., 4522 132 73351, 2008, pp. 1-2.

*Primary Examiner* — David E Smith
(74) *Attorney, Agent, or Firm* — Oblon, McClelland, Maier & Neustadt, L.L.P.

(57) ABSTRACT

In an X-ray computer tomographic apparatus according to an embodiment, an image processing unit generates a projection image and a sectional image based on projection data generated from output of an X-ray detector. When at least one end of a scan range of second scan is set on part of a projection image generated based on projection data acquired through first scan by the image processing unit, a scan plan processing unit displays a sectional image corresponding to at least one end of the scan range among sectional images generated based on projection data acquired through the first scan by the image processing unit.

20 Claims, 21 Drawing Sheets

(51) Int. Cl.
*A61B 6/06* (2006.01)
*G09B 23/28* (2006.01)

(52) U.S. Cl.
CPC ............ *A61B 6/4085* (2013.01); *A61B 6/463* (2013.01); *A61B 6/465* (2013.01); *A61B 6/466* (2013.01); *A61B 6/469* (2013.01); *A61B 6/488* (2013.01); *A61B 6/50* (2013.01); *A61B 6/5205* (2013.01); *A61B 6/54* (2013.01); *A61B 6/545* (2013.01); *G09B 23/286* (2013.01)

(58) Field of Classification Search
CPC ........... A61B 5/488; A61B 5/54; A61B 5/542; A61B 5/545
See application file for complete search history.

(56) References Cited

U.S. PATENT DOCUMENTS

2008/0205587 A1* 8/2008 Nakanishi .............. A61B 6/032
378/19
2009/0046833 A1 2/2009 Hirokawa et al.
2009/0147909 A1* 6/2009 Yoda ........................ A61B 6/04
378/4

FOREIGN PATENT DOCUMENTS

JP 2009-142300 A 7/2009
JP 2009-285147 A 12/2009
WO WO 2007/032462 A1 3/2007

\* cited by examiner

FIG.3
CASE OF HELICAL SCAN
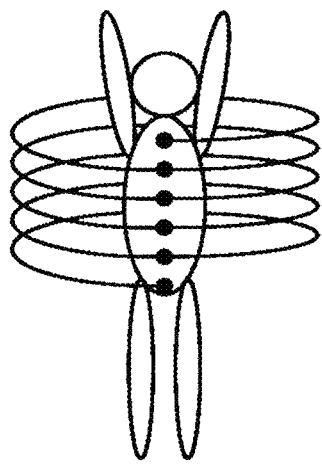
SYNTHESIZE AND DISPLAY PROJECTION IMAGE
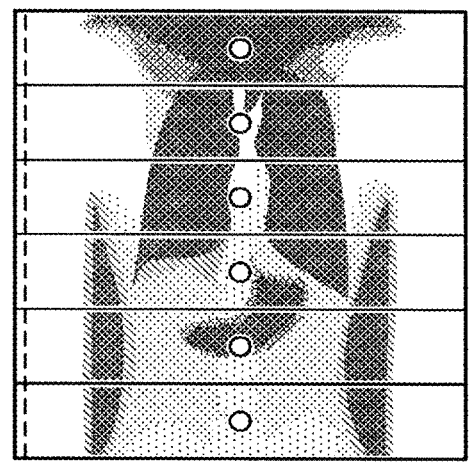
FIG.4
CASE OF NON-HELICAL SCAN
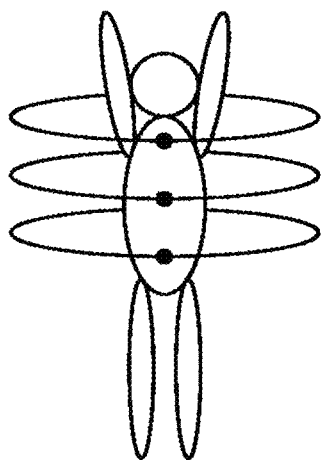
SYNTHESIZE AND DISPLAY PROJECTION IMAGE
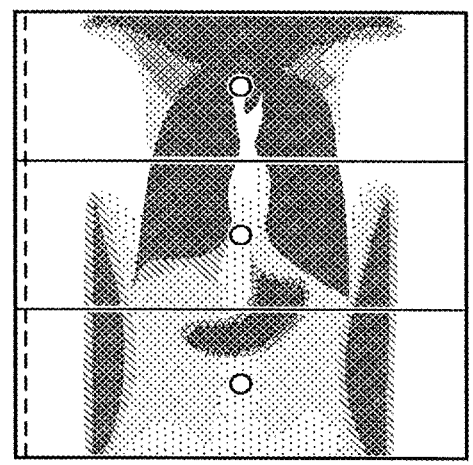

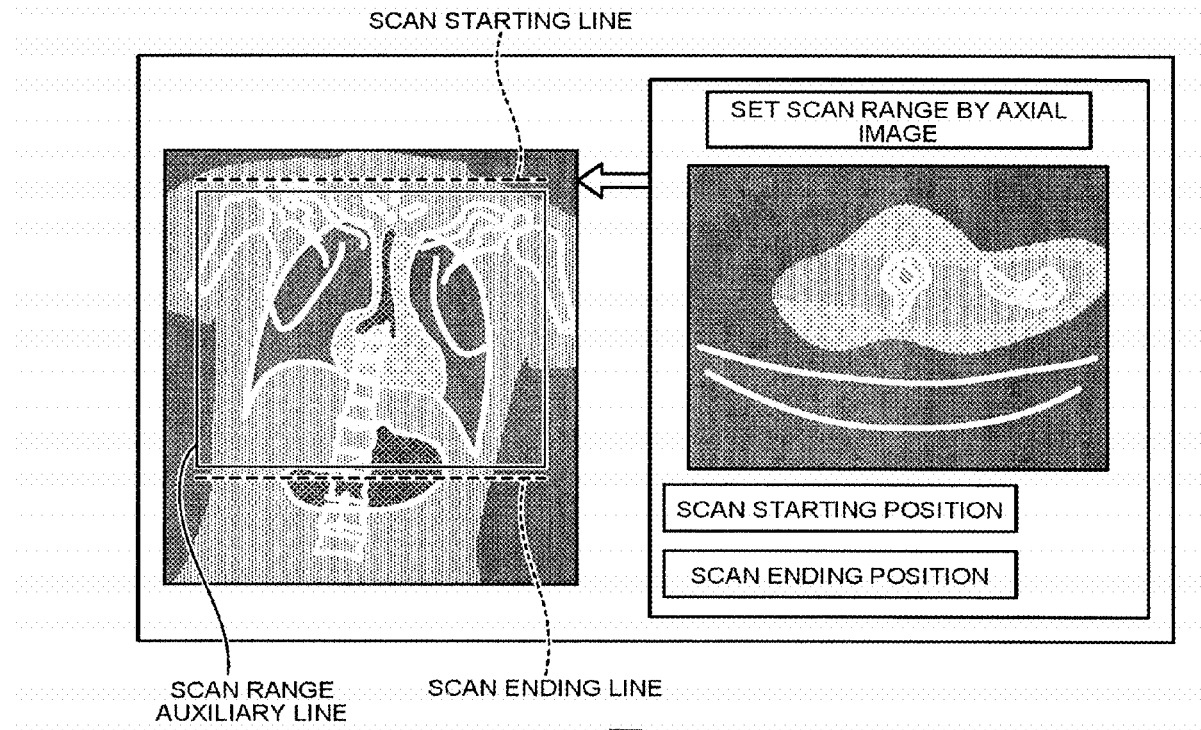
FIG. 9A1
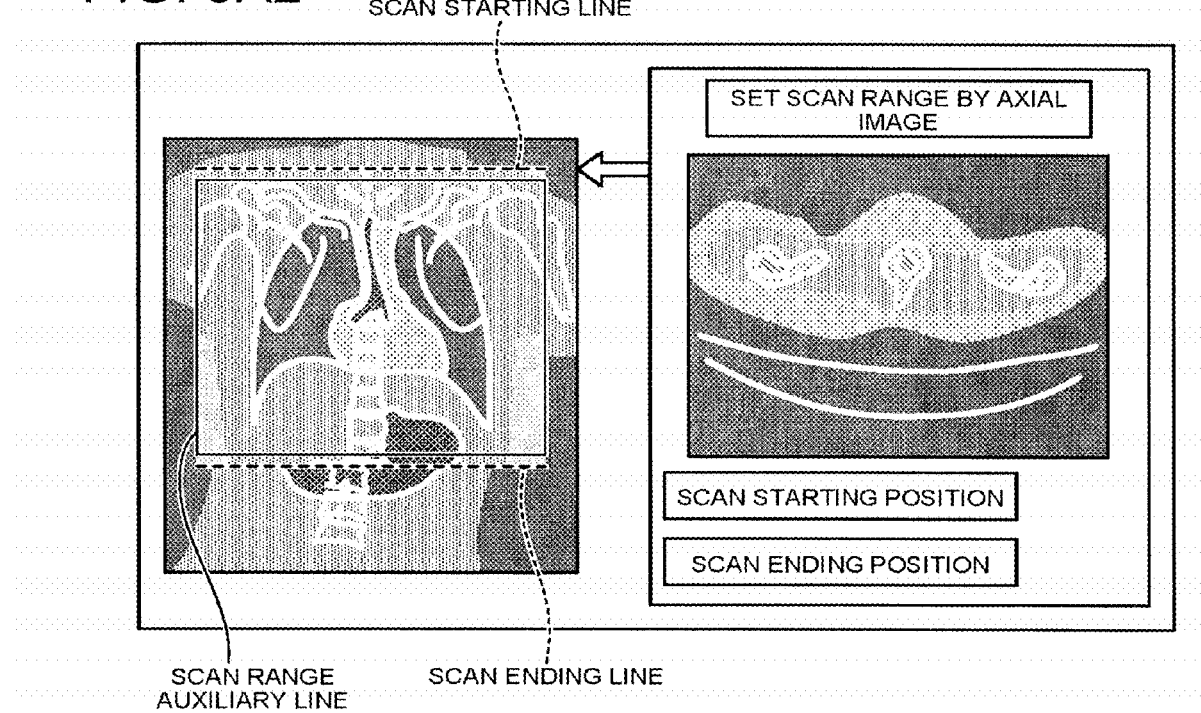
FIG. 9A2

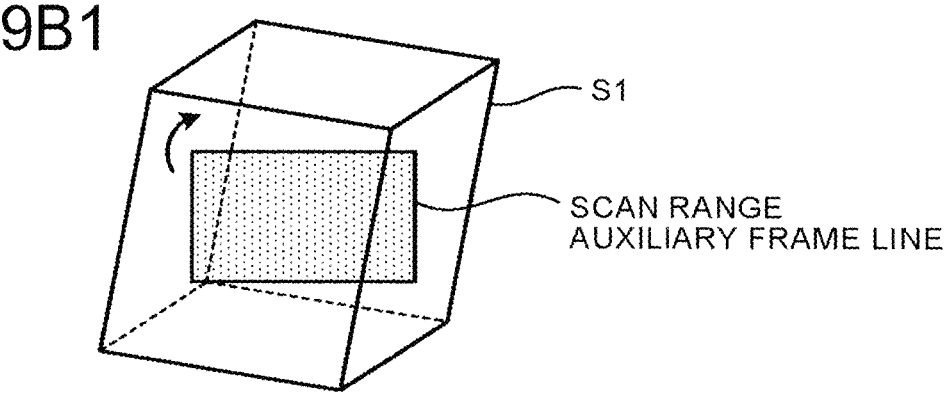
FIG. 9B1
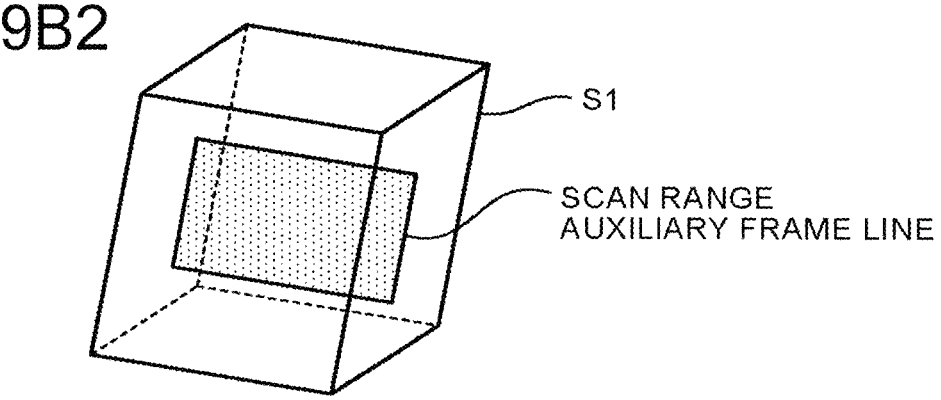
FIG. 9B2
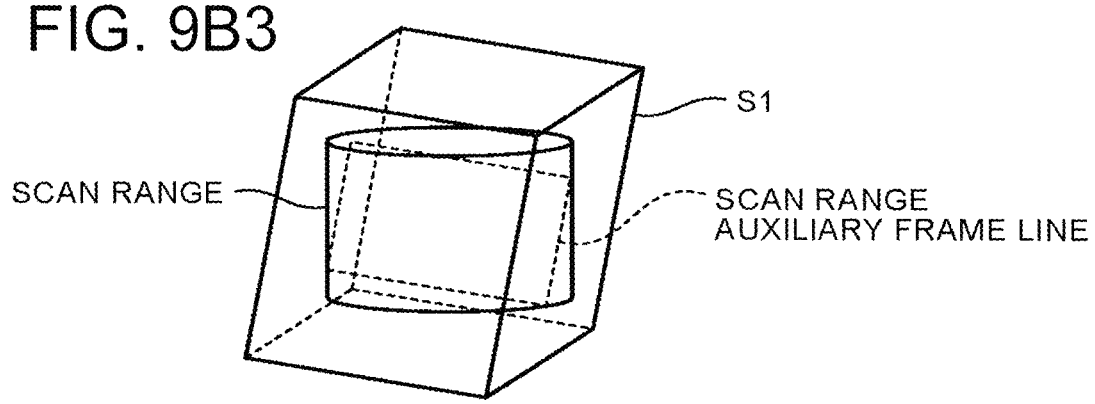
FIG. 9B3

FIG. 10A1
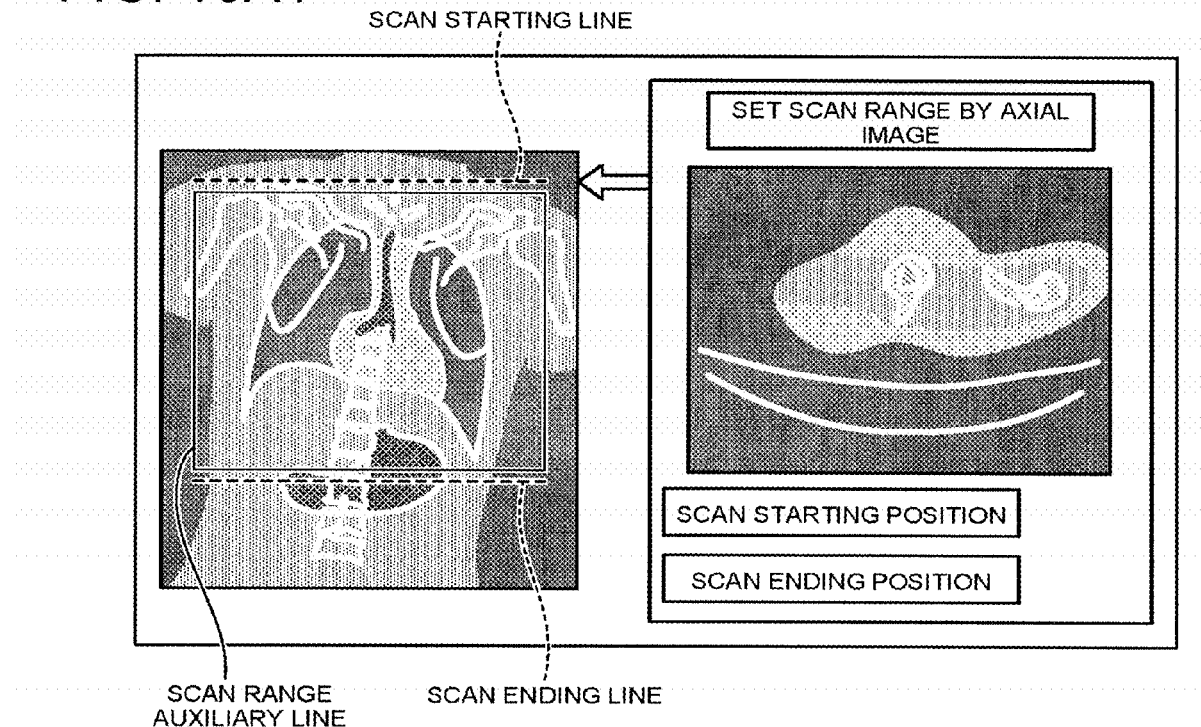
FIG. 10A2
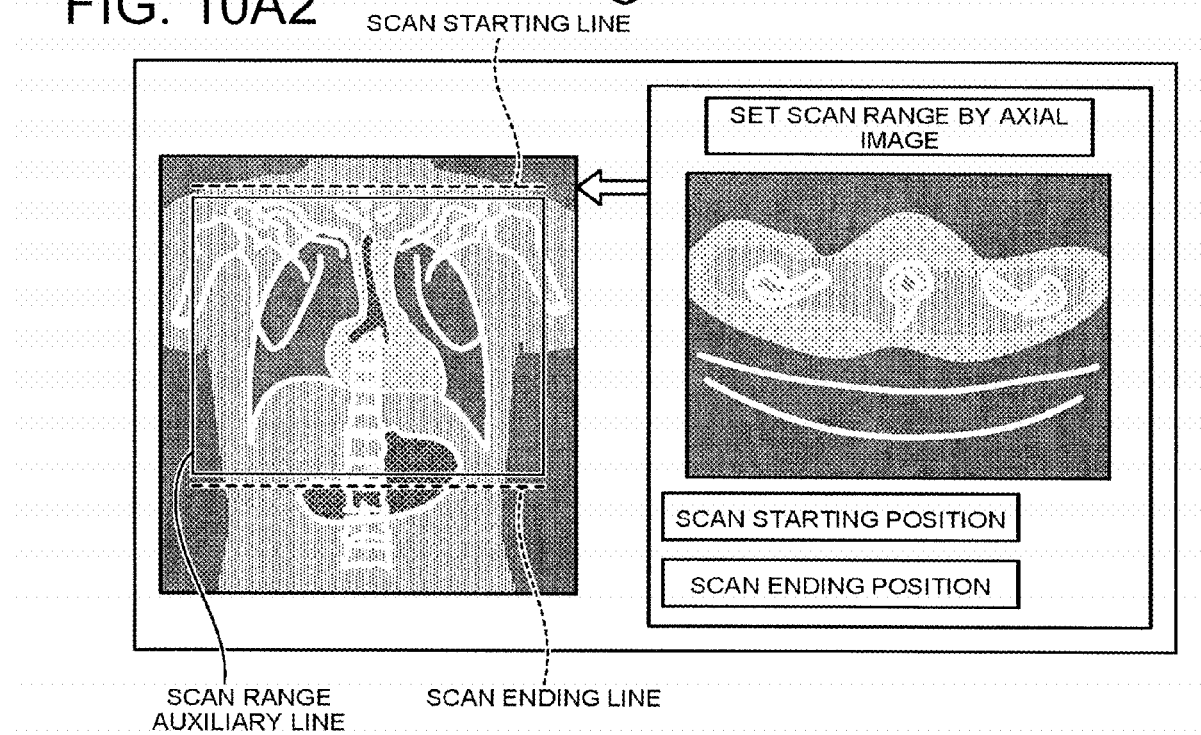

FIG. 10B1
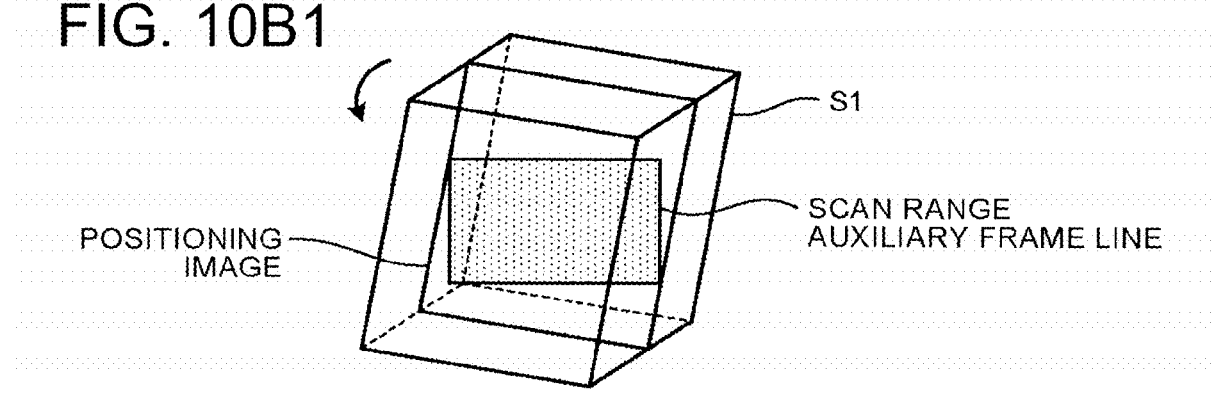
FIG. 10B2
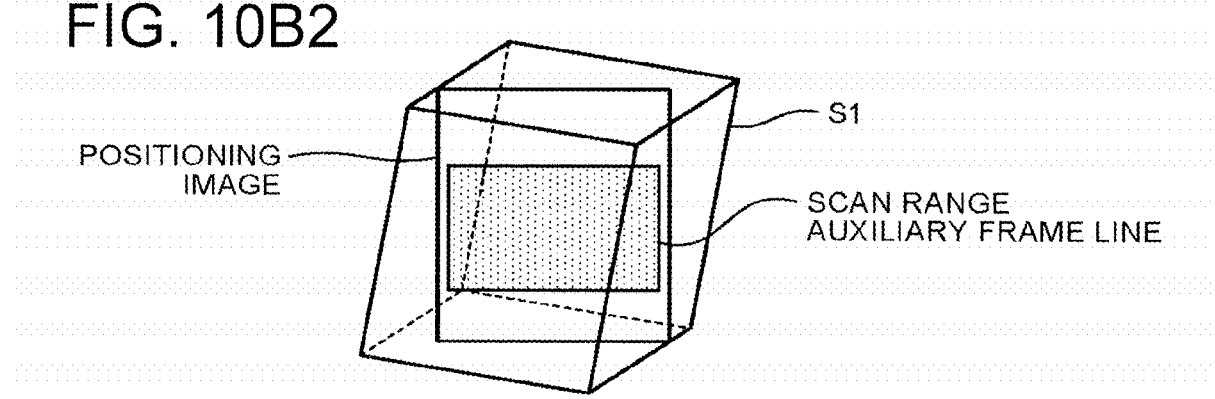
FIG. 10B3
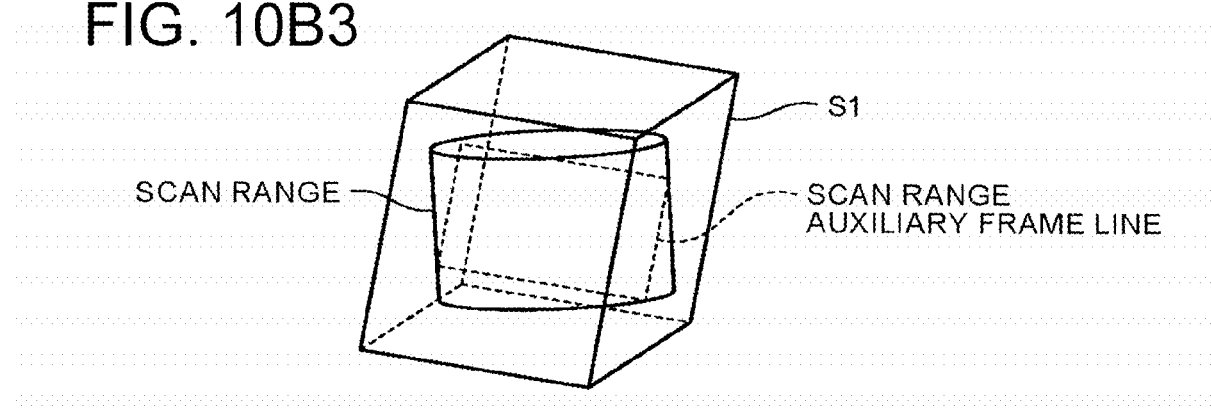

X-RAY COMPUTER TOMOGRAPHIC APPARATUS AND SCAN PLAN SETTING SUPPORTING APPARATUS

CROSS-REFERENCE TO RELATED APPLICATION(S)

This application is based upon and claims the benefit of priority from Japanese Patent Application No. 2014-87762, filed on Apr. 21, 2014, the entire contents of all of which are incorporated herein by reference.

FIELD

Embodiments described herein relate generally to an X-ray computer tomographic apparatus (X-ray CT) and a scan plan setting supporting apparatus.

BACKGROUND

By virtue of recent progress of low-dose photography, a radiation dose in full scan used for diagnosis is increasingly lowering. In order to determine a scan position and range and a reconstruction position and range of the full scan and calculate an optimum radiation dose in a scan planning stage, two-dimensional positioning images (also called positioning image scanograms) are photographed. The positioning image is photographed by repeating photographing continuously while moving a top board at a constant speed or intermittently or intermittently in sync with the movement of the top board with an X-ray tube fixed at a 0° position, that is, the front position with respect to a subject, for example. Although the positioning image may be collected from, in addition to the front direction, two side directions and further certain directions, a display direction is fixed to the photographing position, and the display direction cannot be changed after photographing.

An exposure dose required for photographing the positioning image has not been much changed in spite of a recent reduction in an exposure dose of the full scan. There is a problem in that automatic exposure control used in CT scan (CT-AEC), if the height of a bed changes, changes calculated mA even for the same subject due to a magnification. The positioning image is merely a projection image (also called a projection image) and is not much favorable in the setting accuracy and the convenience of setting operation of a scan range or the like in scan planning.

BRIEF DESCRIPTION OF THE DRAWINGS

FIG. 3 is a diagram illustrating a projection image generated from helical scan data in Step S16 in FIG. 2;

FIG. 4 is a diagram illustrating a projection image generated from non-helical scan data in Step S16 in FIG. 2;

FIG. 9A1 is a diagram for illustrating an example of changing a projection direction in a scan range according to the present embodiment;

FIG. 9A2 is a diagram for illustrating an example of changing a projection direction in a scan range according to the present embodiment;

FIG. 9B1 is a diagram for illustrating an example of changing the projection direction in the scan range according to the present embodiment;

FIG. 9B2 is a diagram for illustrating an example of changing the projection direction in the scan range according to the present embodiment;

FIG. 9B3 is a diagram for illustrating an example of changing the projection direction in the scan range according to the present embodiment;

FIG. 10A1 is a diagram for illustrating an example of changing a projection direction in the entire projection image according to the present embodiment;

FIG. 10A2 is a diagram for illustrating an example of changing a projection direction in the entire projection image according to the present embodiment;

FIG. 10B1 is a diagram for illustrating an example of changing the projection direction in the entire projection image according to the present embodiment;

FIG. 10B2 is a diagram for illustrating an example of changing the projection direction in the entire projection image according to the present embodiment;

FIG. 10B3 is a diagram for illustrating an example of changing the projection direction in the entire projection image according to the present embodiment;

DETAILED DESCRIPTION

Figure 1:
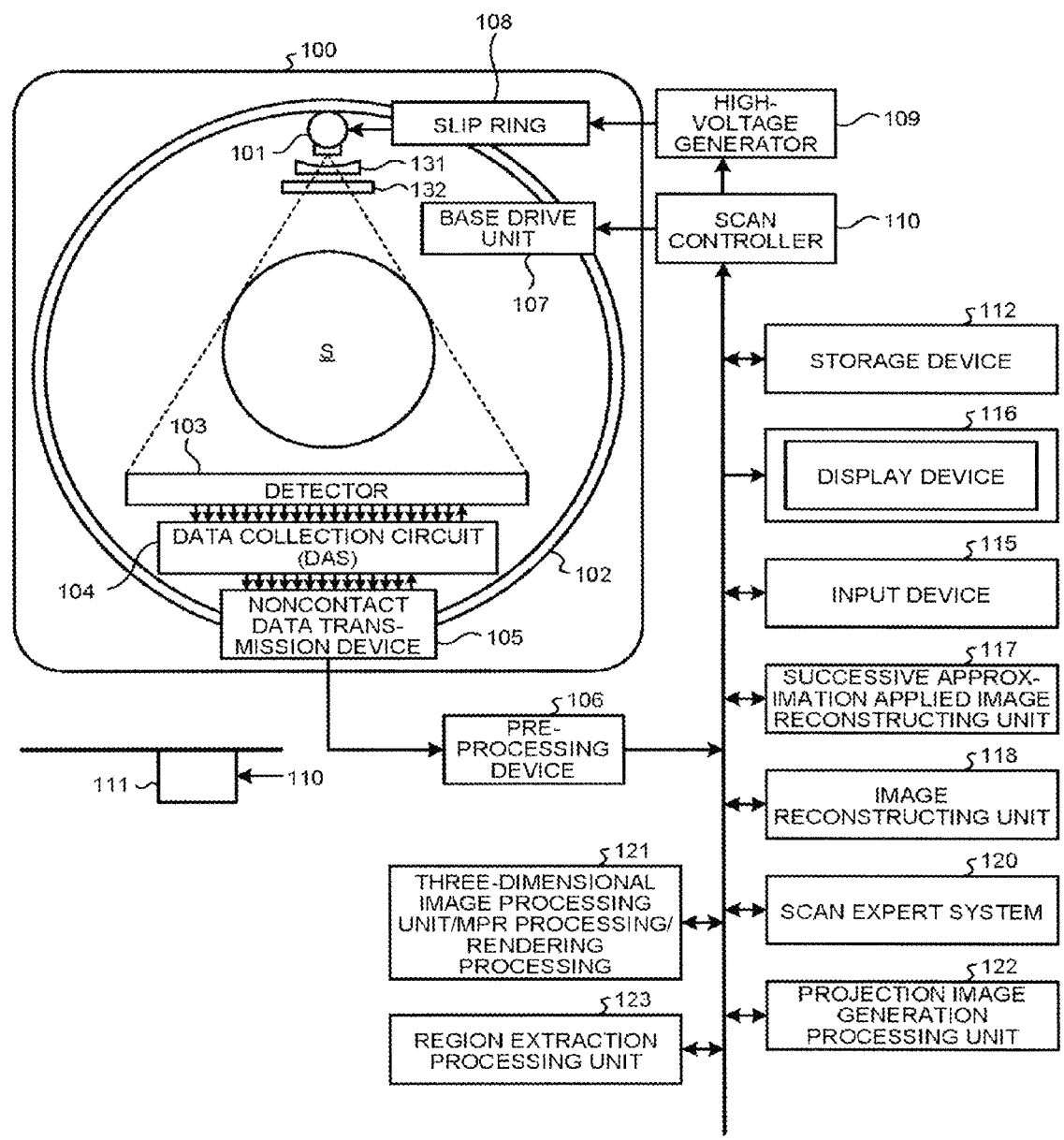
FIG. 1 is a diagram illustrating the configuration of an X-ray computer tomographic apparatus according to an embodiment.

According to an embodiment, An X-ray computer tomographic apparatus includes an X-ray tube, a high-voltage generator, an X-ray detector, a rotational frame and processing circuitry. The high-voltage generator configured to generate a tube voltage to be applied to the X-ray tube. The X-ray detector configured to detect X-rays emitted by the X-ray tube and having passed through a subject. The rotational frame configured to support the X-ray tube rotatably around the subject. The processing circuitry configured to control the high-voltage generator and the rotational frame in order to perform first scan and second scan on the subject. The processing circuitry configured to generate a projection image and a sectional image based on projection data generated from output of the X-ray detector. The processing circuitry configured to, when at least one end of a scan range of the second scan is set on part of a projection image generated based on projection data acquired through the first scan, display a sectional image corresponding to at least one end of the scan range among sectional images generated based on the projection data acquired through the first scan.

The following describes an X-ray computer tomographic apparatus and a scan plan setting supporting apparatus according to the present embodiment with reference to the drawings.

The X-ray computer tomographic apparatus according to the present embodiment includes an X-ray tube, a high-voltage generator that generates a tube voltage to be applied to the X-ray tube, an X-ray detector, a bed on which a subject is mounted, a rotational mechanism that supports the X-ray tube and the X-ray detector rotatably around the subject, and a storage unit that stores therein projection data generated from output of the X-ray detector. Based on the projection data, a reconstruction processing unit reconstructs volume data. A sectional image generation processing unit generates sectional images from the volume data. A projection image generation processing unit generates projection images (also called projection images) from the projection data.

A scan plan processing unit constructs a scan planning screen containing the sectional image and the projection image. An auxiliary frame line indicating a scan range is superimposed on the projection image. A display unit displays the scan planning screen. An operator operates an operating unit to move and enlarge or reduce the auxiliary frame line on the projection image. A controller controls the high-voltage generator, the bed, and the rotational mechanism to perform full scan in accordance with a scan plan set on the scan planning screen. The sectional image includes, for example, axial images, coronal images, sagittal images, and oblique images. Respective axial images, for example, are generated for a scan starting position and a scan ending position following the operation of the movement and enlargement or reduction of the auxiliary frame line.

Volume data collected by performing volume scan on the subject is used for the scan plan, thereby enabling visual confirmation of any projection image and an axial image, for example, of any position and improving the setting accuracy and the convenience of setting operation of the scan range or the like.

The present embodiment performs scan planning using the volume data obtained by performing helical scan, volume scan, or the like before the full scan, thereby enabling the setting accuracy and the convenience of setting operation to be improved. In this situation, the volume data may be collected with a plurality of pieces of energy using Dual Energy by the kV switching or the like. This processing can remarkably increase the amount of information to be obtained compared to that of a conventional projection image (a positioning image) photographed from one direction or two directions and can impart sufficient information to scan plan formulation of the full scan. This processing can also accurately ascertain the range and position of target organs or the like of the subject within the scan range and can also automatically set the scan range for organs to be scanned. Obtaining three-dimensional information also reveals absorbed doses of respective pieces of tissue of the subject, and an appropriate tube current (mA), which is necessary and not excessive, can also be selected with high precision.

The accuracy of the setting (presetting) of a scan position and range of full scan is increased in a scan planning stage, thereby enabling a workflow of the entire examination including scout scan (also called positioning scan), the full scan, and image interpretation to be improved and also improving examination throughput.

FIG. 1 is a diagram illustrating the configuration of the X-ray computer tomographic apparatus according to the present embodiment. The X-ray computer tomographic apparatus includes various types including the rotate/rotate type, in which an X-ray tube 101 and an X-ray detector 103 integrally rotate around the subject about a rotational axis and the stationary/rotate type, in which many detection elements are arranged in a ring shape and only the X-ray tube 101 rotates around the subject, any of which can be used. The following describes a case of being the rotate/rotate type, which is currently in the mainstream. In order to reconstruct one slice of tomographic image data, projection data of one round of the circumference of the subject, that is, about 360° is required. Even the half-scan method requires projection data of 180° plus a view angle. The present invention can be applied to both the methods of reconstruction. The mainstream of a mechanism to convert incident X-rays into electric charges includes the indirect conversion type, in which a phosphor such as a scintillator converts X-rays into light and then converts the light into electric charges by a photoelectric conversion element such as a photodiode, and the direct conversion type, which uses generation of electron-hole pairs within a semiconductor by X-rays and their movement to an electrode, that is, the photoconductive phenomenon. An X-ray detection element may be any of those, and the following describes a case of being the former, or the indirect conversion type. Recent years have seen advances in development into products of the X-ray computer tomographic apparatus of, what is called, the multi-tube type, which installs a plurality of pairs of an X-ray tube and an X-ray detector in a rotational ring and advances in the development of its peripheral technology. The present invention can be applied to both the conventional single-tube type X-ray computer tomographic apparatus and the multi-tube type X-ray computer tomographic apparatus. The following describes a case of being the single-tube type.

The X-ray computer tomographic apparatus according to the present embodiment includes a gantry 100. The gantry 100 includes an annular rotational frame 102. The rotational frame 102 constitutes a rotational mechanism together with a base drive unit 107. The rotational frame 102 is driven by the base drive unit 107 to rotate about a rotational axis RA. The rotational frame 102 installs the X-ray tube 101 and the X-ray detector 103 so as to face each other. At the time of scan, the subject mounted on a top board of a bed 111 is inserted into between the X-ray tube 101 and the X-ray detector 103. The top board is moved forward and backward in its longitudinal direction by a drive unit (not illustrated) installed within the bed 111.

The X-ray tube 101 receives application of a tube voltage and supply of a filament current from a high-voltage generator 109 via a slip ring 108 to generate X-rays. The X-ray detector 103 includes a plurality of X-ray detection elements that detect X-rays having passed through the subject and output electric signals reflecting the radiation dose of the incident X-rays. The X-ray detection elements are, for example, arranged in a manner of 320 rows×912 channels.

A data collection circuitry 104 collects signals output from the X-ray detector 103 and converts them into digital signals (called purely raw data). The data collection circuitry 104 is connected to a pre-processing device 106 via a noncontact data transmission device 105. The pre-processing device 106 performs processing such as sensitivity correction and logarithmic conversion on the purely raw data to generate projection data. The projection data is stored in a storage device 112.

As illustrated in FIG. 1, the gantry 100 includes a bow tie filter 131 and a collimator 132 between the X-ray tube 101 and the X-ray detector 103. The bow tie filter 131 is an X-ray filter for adjusting an X-ray quantity emitted from the X-ray tube 101. Specifically, the bow tie filter 131 is a filter that passes and attenuates the X-rays emitted from the X-ray tube 101 so that X-rays applied from the X-ray tube 101 to the subject P has predetermined distribution. The bow tie filter 131 is, for example, a filter formed of aluminum so as to have a certain target angle and a certain thickness. The collimator 132 is a slit for narrowing an irradiation range of the X-rays whose X-ray quantity has been adjusted by the bow tie filter 131.

A scan controller 110 performs the entire control on the X-ray computer tomographic apparatus. The scan controller 110, for example, controls respective operations of the base drive unit 107, the high-voltage generator 109, and the bed 111 in order to perform scan in accordance with scan planning information described below. Specifically, the scan controller controls respective operations for performing first scan (the positioning scan) and second scan (the full scan) on the subject. The scan controller 110 controls operations based on various instructions input via an input device 115 and display processing of various information (a scan plan supporting screen, for example) on a display device 116. The scan controller 110 controls the respective units included in the X-ray computer tomographic apparatus, thereby controlling various pieces of processing performed by the respective units.

An image reconstructing unit 117 is provided to reconstruct image data with relatively low noise based on projection data collected by scanning with low-dose X-rays of the same level as that for conventional photographing of two-dimensional positioning images. A process of reconstruction by the image reconstructing unit 117 is any process having relatively high applicability to noise reduction. Image reconstruction applying the successive approximation (successive approximation applied image reconstruction) is used, for example. Although the following describes reconstruction of volume data by the image reconstructing unit 117 using the successive approximation applied image reconstruction, the successive approximation applied image reconstruction is not limiting as described above.

The image reconstructing unit 117 reconstructs image data, or the volume data in this example, based on the projection data stored in storage device 112 by an algorithm by successive approximation applied reconstruction. The volume data is stored in the storage device 112. Although successive approximation applied reconstruction processing is essentially applied to the reconstruction of the positioning image (tomographic data or volume data) used in the scan planning of the full scan before the full scan, the successive approximation applied reconstruction processing is selectively applied in relation to reconstruction processing of another process of a reconstruction processing unit 118 described below for the reconstruction of image data (tomographic data or volume data) based on projection data collected by the full scan.

The successive approximation applied reconstruction is an application of the successive approximation. The successive approximation is, as is well known, a method for reconstructing an image by comparing the difference between an actually measured value and a calculated value for projection data and repeating corrections. The successive approximation applied reconstruction is a method that adds processing that reduces noise on the projection data and processing that reduces noise in image data in an image reconstruction cycle of the successive approximation. An algorithm of the successive approximation applied reconstruction reduces noise of the collected projection data using a statistical noise model and a scanner model. An anatomical model is further used to determine which is noise and which is real projection data in an image reconstruction domain, extract only a noise component, and repeat this processing, thereby removing or reducing noise with high precision. The successive approximation applied reconstruction is reconstruction that achieves both low-dose photographing and high image quality with low-noise.

The reconstruction processing unit 118 reconstructs the volume data by a method different from the successive approximation applied image reconstruction by the image reconstructing unit 117 such as the Feldkamp method and the cone-beam reconstruction based on projection data within the range of a view angle of 360° or 180° plus a fan angle. The Feldkamp method is reconstruction when a projection ray crosses a reconstruction plane such as a cone-beam and approximate image reconstruction that performs processing by regarding as a fan projection beam at the time of convolution on the precondition that a cone angle is small and that performs processing on reverse projection along a ray at the time of scanning. The cone-beam reconstruction is reconstruction, as a method that can reduce cone angle errors compared to the Feldkamp method, and correct projection data in accordance with the angle of a ray with respect to a reconstruction plane. The volume data is stored in the storage device 112.

In order to reconstruct the volume data from the projection data collected through the positioning scan, a method having high applicability to noise reduction such as the successive approximation applied reconstruction is applied. In order to reconstruct the volume data from the projection data collected through the full scan, a method different from that of the positioning scan, such as the successive approximation applied reconstruction, the Feldkamp method, and the cone-beam reconstruction, is selected as required.

The display device 116 is provided to mainly display images generated from the volume data and display the scan planning screen constructed by a scan expert system 120. The input device 115 includes a keyboard, a mouse, and the like for receiving input of instructions by the operator.

A three-dimensional image processing unit 121 has functionality to generate data of three-dimensional images from the volume data stored in the storage device 112 through volume rendering processing and functionality to generate data of sectional images about an axial/sagittal/coronal or any oblique section from the volume data through section conversion processing (MPR processing). A projection image generation processing unit 122 generates data of a projection image as the positioning image from the projection data stored in the storage device 112. When any view angle is selectively designated from 0°, 45°, and 90° on the scan planning screen, for example, pieces of projection data collected when the X-ray tube 101 is positioned at the view angle under the control of the scan expert system 120 are read from the storage device 112. The projection image generation processing unit 122 arranges the pieces of read projection data of the same view angle in accordance with their respective top board positions and synthesizes them into one, thereby generating data of the positioning image, that is, the positioning image equivalent to a conventional one.

A region extraction processing unit 123 extracts an organ region from the volume data stored in the storage device 112. The region extraction processing unit 123, for example, receives a code of an organ to be examined contained in examination request information from the scan expert system 120 and extracts the organ region from the volume data in accordance with a threshold to be applied to the organ to be examined. Without being limited to the threshold processing, the organ region may be identified by performing segmentation on organs through matching processing with a standard anatomical model. Information on the extracted organ region is supplied to the scan expert system 120. The scan expert system 120 initially sets a scan range in a range surrounding the extracted organ region. The organ region may be extracted with the three-dimensional image, sectional image, or the positioning image as an object of the threshold processing.

The scan expert system 120, in order to support setting of a scan plan by a user, selects a plurality of scan plan candidates suitable for an examination object, an organ to be examined, the age and sex of the subject, and the like contained in the examination request information and constructs a list of the scan plan candidates together with examination request details on the scan planning screen. The scan expert system 120 initially sets the scan range surrounding the extracted organ region and forms an auxiliary frame line indicating the scan range. The scan planning screen contains the sectional image and the positioning image. The auxiliary frame line indicating the scan range is superimposed on the positioning image of the scan planning screen. Although the auxiliary frame line indicating the scan range is initially set with size containing the extracted organ region, its size and position are freely changed in accordance with operations such as dragging of the input device 115 by the user. This operation enables a three-dimensional scan plan, which has been conventionally impossible, to be performed. The scan expert system 120 supplies position information defining a scan starting position of the scan range indicated by the auxiliary frame line and position information defining a scan ending position of the scan range to the three-dimensional image processing unit 121. The section conversion functionality of the three-dimensional image processing unit 121 generates an axial image of a section orthogonal to the rotational axis (that nearly matches an anteroposterior axis) at the scan starting position from the volume data and similarly generates an axial image of a section orthogonal to the rotational axis (that nearly matches the anteroposterior axis) at the scan ending position from the volume data. These axial images are displayed together with the positioning image of the scan planning screen.

The scan expert system 120 calculates a recommended value corresponding to the body thickness of the subject, the size of the organ to be examined, or the like that can identify a tube current (mA) and the like in the scan plan candidates with high precision from the volume data. A recommended value of the tube current (mA) can also be freely changed in accordance with an operation on the input device 115 by the user. A tube voltage, a slice thickness, a reconstruction function, and the like are designated on the scan planning screen. The scan expert system 120 generates the scan plan information in accordance with the determined scan plan. The scan plan information is sent to the scan controller 110, and the full scan is performed in accordance with the scan plan information under the control of the scan controller 110.

Figure 2:
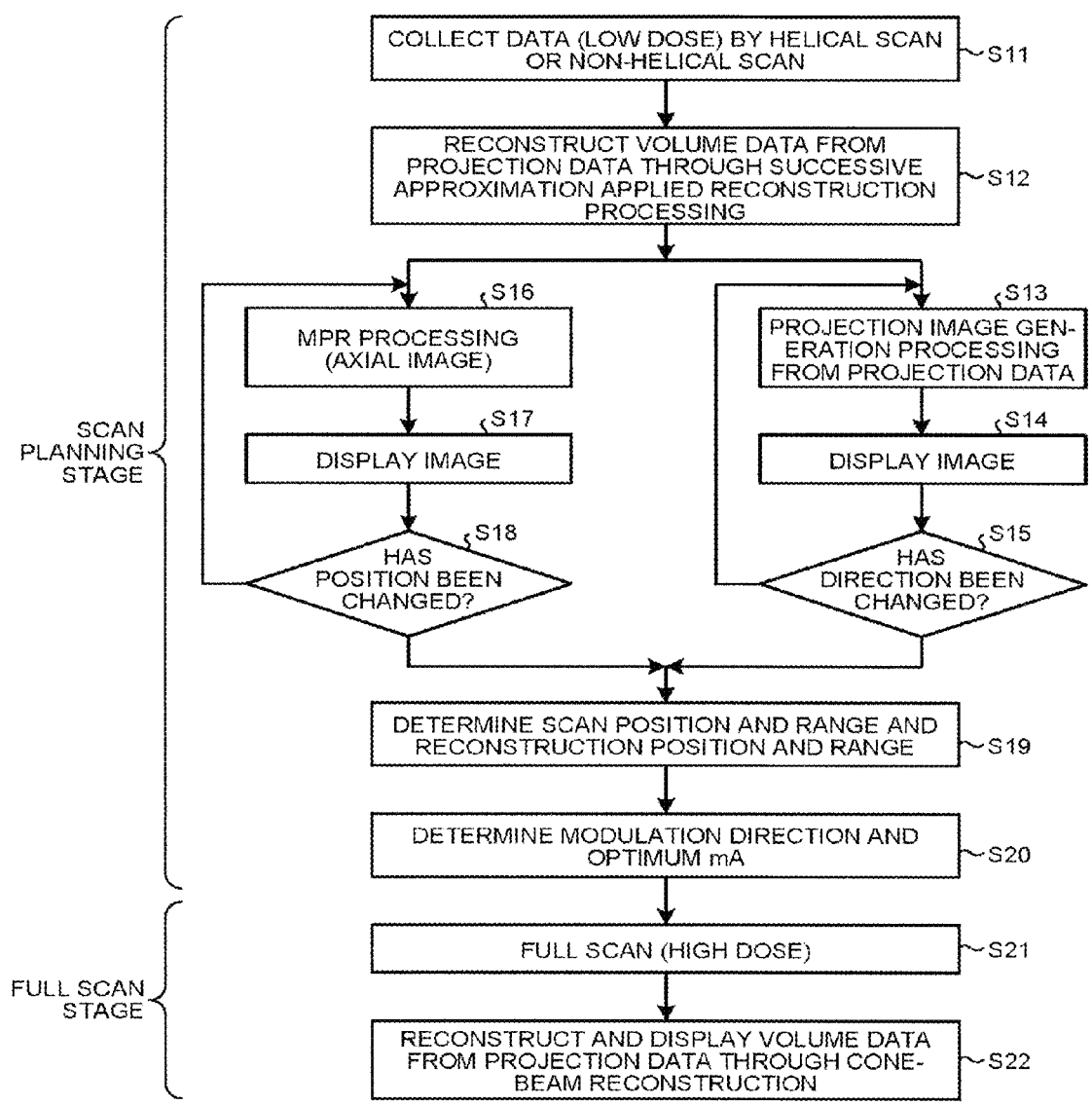
FIG. 2 is a diagram illustrating a processing procedure for the entire CT examination by the present embodiment.

FIG. 2 illustrates a processing procedure of the entire CT examination from the low-dose scout scan in the scan planning stage through the full scan finally up to image display by the present embodiment. In the scan planning stage, first, the scout scan is performed on a relatively wide area such as the entire chest, the entire abdomen, and the entire upper-body of the subject with a lower radiation dose than that of the full scan by the helical scan or non-helical scan under the control of the scan controller 110. In the non-helical scan, each time pieces of projection data of one round are collected, the top board moves by a distance corresponding to a cone divergence angle, the pieces of projection data of one round are collected at the position, and such an operation is repeated. The pieces of projection data of 360° are collected through the scout scan (S11). The image reconstructing unit 117 reconstructs the volume data based on the pieces of projection data collected through this scout scan (S12). The volume data is stored in the storage device 112.

Figure 7:
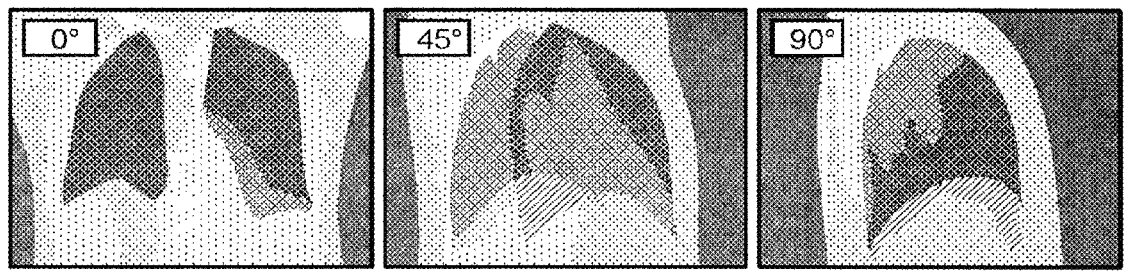
FIG. 7 is a diagram illustrating an example of three-directional projection images generated by the projection image generation processing unit in FIG. 1.

Among the pieces of projection data of the entire circumference collected through the scout scan, pieces of projection data collected at an angle selected from 0°, 45°, and 90° of the X-ray tube 101 as appropriate via the input device 115 are read from the storage device 112 to the projection image generation processing unit 122. The pieces of read projection data are arranged in accordance with top board positions (positions in the anteroposterior axial direction) and are synthesized into one. This processing generates data of the positioning image (projection image) viewed from one direction as exemplified in FIG. 7 (S13). The 0° positioning image is initially generated and is displayed on the scan planning screen as exemplified in FIG. 5 (S14). When the other 45° or 90° projection direction is selected via the input device 115 (S15), control returns to the step S13, where the other selected 45° or 90° positioning image is generated, and the scan planning screen is switched to display the image (S15).

FIG. 3 illustrates the synthesis of the positioning image (projection image) when the scout scan is performed by the helical scan, whereas FIG. 4 illustrates the synthesis of the positioning image when the scout scan is performed by the non-helical scan. Because the present embodiment collects the pieces of projection data of the entire circumference by the scan, the positioning image can be generated at any direction. The example of selecting any of 0°, 45°, and 90° as the projection direction includes that any angle can be set.

Figure 5:
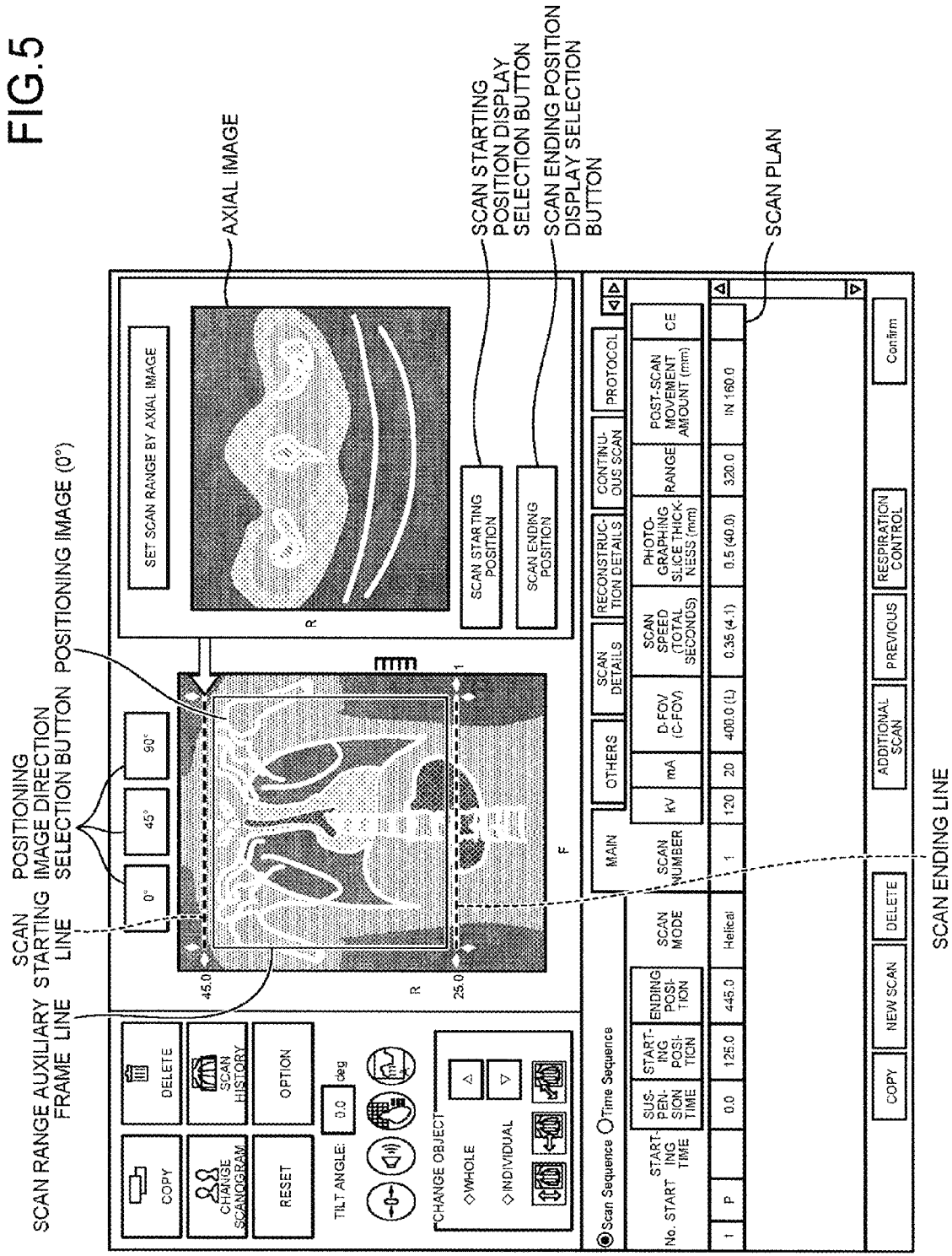
FIG. 5 is a diagram illustrating a scan plan setting screen configured by the scan expert system in FIG. 1, which is an example of displaying an axial image at a scan starting position.

The region extraction processing unit 123 extracts the region of the organ to be examined from the volume data. The scan expert system 120 initially sets a cylindrical scan area with the rotational axis as a central axis so as to surround the extracted region of the organ to be examined. The scan expert system 120 supplies information on a scan starting position and a scan ending position of the scan area to the three-dimensional image processing unit 121. The three-dimensional image processing unit 121 generates an axial image of a section about the scan starting position of the scan range and generates an axial image about the scan ending position (S16). These axial images are displayed on the scan planning screen as illustrated in FIG. 5 (S17). The axial images are not limiting, and images of any other sections may be displayed. One section is not limiting, and multiple sections (MPR) may display images.

If the size or position of the auxiliary frame line indicating the scan range superimposed on the positioning image on the scan planning screen has been changed in accordance with operations such as dragging of the input device 115 by the user (S18), the scan expert system 120 changes the position or size of the auxiliary frame line on the screen and immediately supplies position information defining a scan starting position of the changed scan range and position information defining a scan ending position of the changed scan range to the three-dimensional image processing unit 121. The three-dimensional image processing unit 121 generates (S16) and displays (S17) an axial image at the changed scan starting position and an axial image at the changed scan ending position from the volume data. When the auxiliary frame line is thus moved and enlarged or reduced, the axial image at the scan starting position and the axial image at the scan ending position by the scan range changed along therewith are generated and displayed accordingly. The user, when setting and adjusting the scan range, can check the scan starting position and the scan ending position by the respective axial images.

Figure 6:
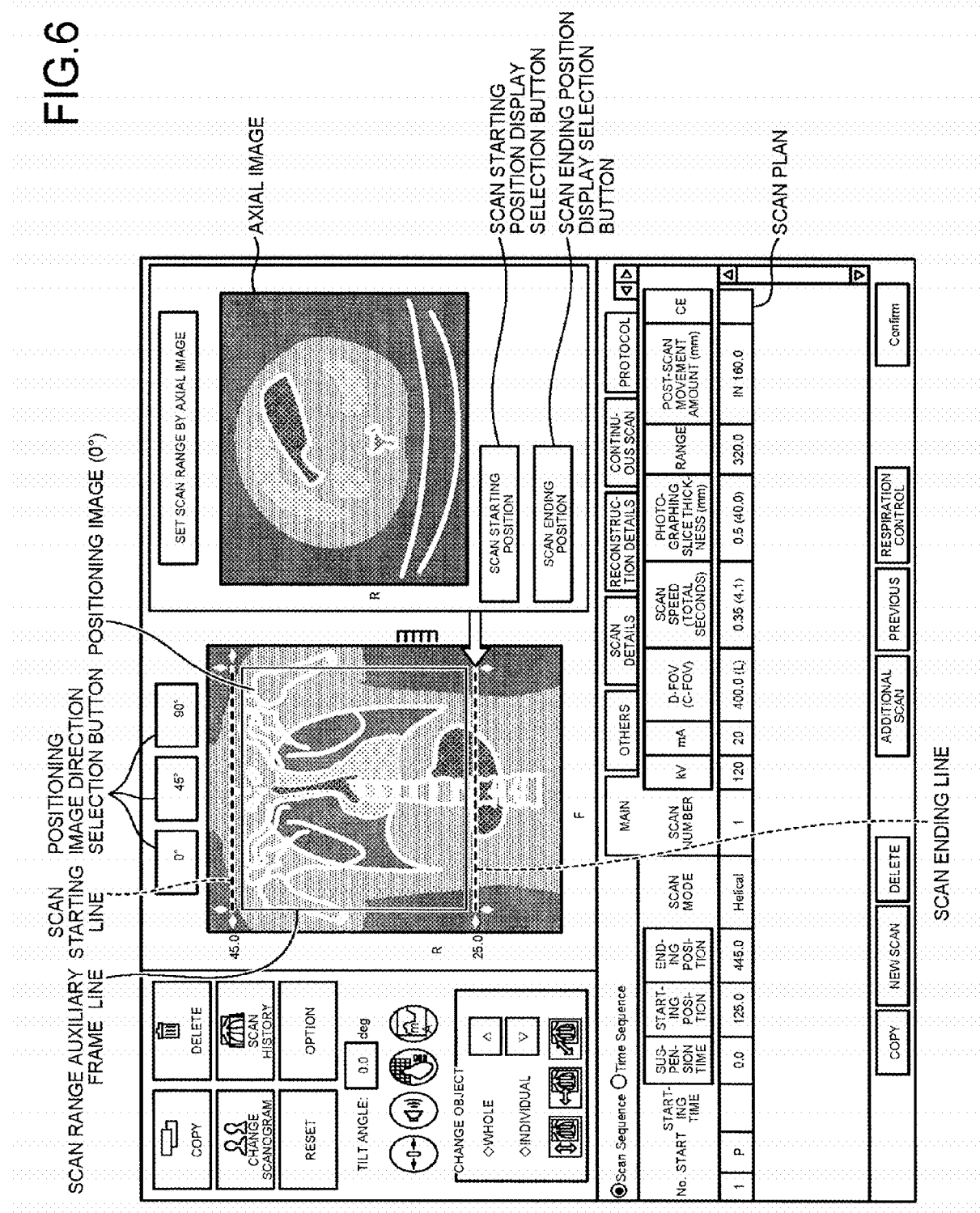
FIG. 6 is a diagram illustrating the scan plan setting screen configured by the scan expert system in FIG. 1, which is an example of displaying an axial image at a scan ending position.

FIG. 5 and FIG. 6 illustrate scan plan supporting screens constructed by the scan expert system 120. The scan plan supporting screen displays scan conditions in a scan plan numerically. Expressed individually numerically are recommended values of scan starting time, suspension time, scan starting position, scan ending position, scan mode, scan number, tube voltage (kV), tube current (mA), scan range (C-FOV), reconstruction range (D-FOV), scan speed (total time), photographing slice thickness, movement range, post-scan movement amount, and the like, and the user can freely change them. The scan plan supporting screen displays the positioning image, which is the front-direction (0°) positioning image in this example. By selectively pressing the three "positioning image direction selection buttons" to input a desired angle, the display can be switched to the positioning image viewed from another angle.

As described above, the rectangular auxiliary frame line defining the scan range is superimposed on the positioning image. The rectangular auxiliary frame line is accompanied by a scan starting line and a scan ending line having different line types and display colors so as to be distinguished from each other. It is understood that the scan range indicated by the auxiliary frame line matches the scan range (C-FOV) numerically expressed. When one of them is corrected, the other is automatically corrected in a linked manner. The reconstruction range is often set at the same range as the scan range, and hence the auxiliary frame line of the scan range also serves as a reconstruction range auxiliary line defining the reconstruction range. The scan range auxiliary frame line and the reconstruction range auxiliary frame line may be displayed separately.

The axial images at the scan starting position and the scan ending position corresponding to the auxiliary frame line defining the scan range are selectively displayed. As illustrated in FIG. 5, when a "scan starting position display selection button" is pressed, the axial image at the scan starting position is displayed. As illustrated in FIG. 6, when a "scan ending position display selection button" is pressed, the axial image at the scan ending position is displayed; the user can freely switch therebetween. It is understood that the respective axial images at the scan starting position and the scan ending position may be simultaneously displayed.

The above example describes a case of setting the scan starting position and the scan ending position or a reconstruction starting position and a reconstruction ending position by the scan range auxiliary frame line or the reconstruction range auxiliary frame line superimposed on the positioning image. However, embodiments are not so limited, and the scan starting position and the scan ending position or the reconstruction starting position and the reconstruction ending position may be set by dragging and dropping the sectional image onto the positioning image. The following describes an example using the axial image of FIG. 6. The user, for example, observes the axial images while switching them in the anteroposterior axial direction and determines an axial image corresponding to the scan starting position. The user drags and drops the determined axial image onto the positioning image to set the scan starting position. The user then observes the axial images while switching them in the anteroposterior axial direction and determines an axial image corresponding to the scan ending position. The user drags and drops the determined axial image onto the positioning image to set the scan ending position.

The scan expert system 120 can determine whether the position corresponding to the axial image dragged and dropped is a starting position or an ending position, based on the position of the axial image dragged and dropped in the anteroposterior axial direction and arrangement information of the subject with respect to the bed. Alternatively, the scan expert system 120 can determine whether the position corresponding to the axial image dragged and dropped is the starting position or the ending position, based on information on organs identified by matching processing with the standard anatomical model. In other words, the scan expert system 120 determines that the dragged and dropped axial image is an image of which organ and determines whether the position corresponding to the axial image is the starting position or the ending position.

The scan expert system 120 can determine whether the position corresponding to the axial image dragged and dropped is the starting position or the ending position, based on the position at which the axial image has been dragged and dropped. The scan expert system 120, for example, determines that the position corresponding to the axial image dragged and dropped is the starting position if the dragged and dropped position is on the upper side of the positioning image and determines that the position corresponding to the axial image dragged and dropped is the ending position if the dragged and dropped position is on the lower side of the positioning image.

On these axial images and the positioning image, the entire organ region extracted by the region extraction processing unit 123 is superimposed with semitransparent color, or the outer edge of the extracted organ region is superimposed with color. When performing a contrast examination, an ROI is set on a section of a certain blood vessel, and Prep photographing for starting photographing with the timing of an inflow of a contrast medium is performed. Although it is conventionally required to photograph a certain section again, it is not required to collect the photographed section again because the volume data already exists.

The scan range is automatically set on the thus extracted organ region, the scan range auxiliary frame line is operated as needed while checking the result on the axial images and the positioning image, and finally the size and position of the scan range can be determined with high precision (S19). The scan expert system 120 can identify the thickness and a change in the thickness in the anteroposterior axis for each target organ and subject extracted from the volume data with high precision, and an optimum value of the tube current (mA) and its modulation direction can be determined (S20).

Upon determination of the scan plan, the scan expert system 120 generates the scan planning information in accordance with the determined scan plan, and the full scan is performed in accordance with the scan planning information under the control of the scan controller 110 (S21).

Based on the pieces of projection data collected through the full scan, the volume data is reconstructed through the cone-beam reconstruction, for example, and a three-dimensional image is generated by the three-dimensional image processing unit 121 and is displayed on the display device 116 (S22).

Figure 8:
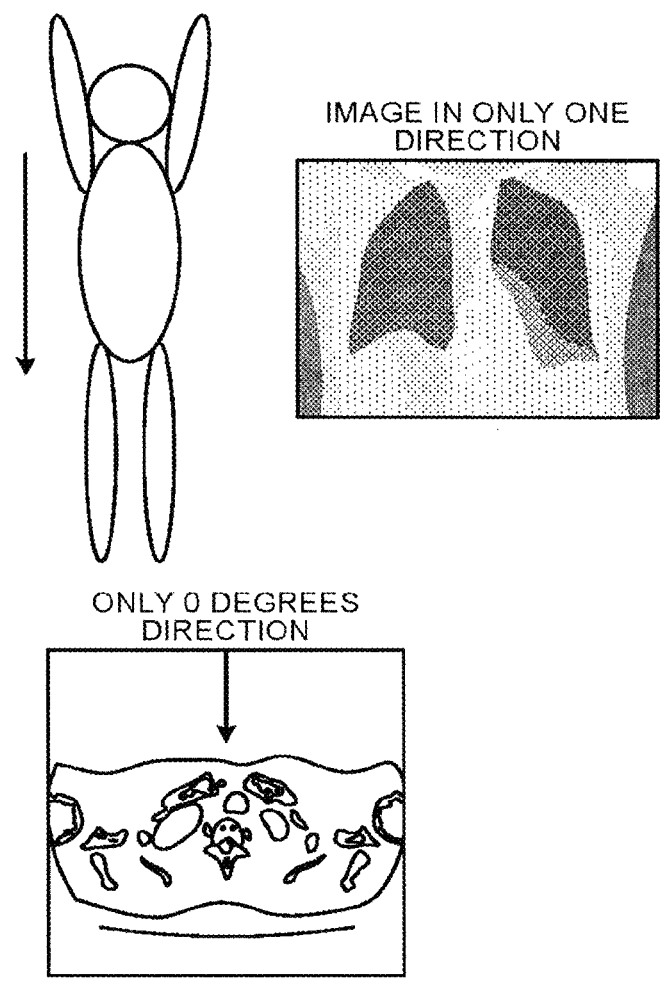
FIG. 8 is a diagram illustrating a one-directional projection image (positioning image) acquired by a conventional method of photographing.

As illustrated in FIG. 8, the positioning image for determining the scan range has been conventionally photographed by emitting X-rays with the X-ray tube not rotated and normally fixed to the 0° direction and simultaneously moving the bed in the Z direction. At the time of scan planning, the scan range and the like are set only from the one-directional positioning image or two-directional positioning images at most. The present embodiment collects the pieces of projection data of 360° directions while rotating the X-ray tube in the same manner as the normal scan, generates the three-dimensional image using the pieces of obtained projection data of all circumferential directions, checks the three-dimensional structure of the target organ or the like, can generate the sectional image at any position and direction, can freely change the direction of the positioning image (projection image), can automatically initially set the scan range by simply extracting the organ region to be examined or the like through the threshold processing owing to that the volume data of CT values is obtained, can check the axial image at the scan starting position and the axial image at the scan ending position, and can, when the position or size of the scan range is changed, check the axial image at the changed scan starting position and the axial image at the changed scan ending position accordingly, thereby enabling the setting accuracy and the convenience of setting operation of the scan range or the like to be improved.

The following describes some embodiments by the above X-ray computer tomographic apparatus. The following embodiments describe in order an embodiment when setting the scan range using the projection image generated based on the pieces of projection data collected through the positioning scan and an embodiment when setting the scan range using the sectional image generated based on the pieces of projection data collected through the positioning scan. The following embodiments are merely examples, and embodiments of the X-ray computer tomographic apparatus according to the present application are not so limited.

First, some embodiments when setting the scan range using the projection image generated based on the pieces of projection data collected through the positioning scan will be described. Although the above embodiment describes an example in which the scan range of the full scan is set by changing the size or position of the auxiliary frame line superimposed on the projection image (positioning image), the scan range can be set by changing the direction of the displayed projection image or auxiliary frame line.

Specifically, the input device 115 receives an operation on the display of the projection image generated based on the pieces of projection data acquired through the first scan (positioning scan). The scan expert system 120 displays the projection image corresponding to the operation received by the input device 115. The scan controller 110 performs control to scan an area contained in the scan range of the second scan in the projection image displayed by the scan expert system 120. The input device 115, for example, receives an operation for changing the projection direction in the entire projection image or the projection direction in the scan range of the second scan (full scan) set in the projection image. The following describes the above embodiment with reference to FIG. 9A1 to FIG. 11B.

FIGS. 9A1, 9A2, 9B1, 9B2 and 9B3 are diagrams for illustrating an example of changing the projection direction in the scan range according to the present embodiment. FIGS. 9A1 and 9A2 illustrate an area of the scan plan supporting screen constructed by the scan expert system 120. As illustrated in FIGS. 9A1 and 9A2, when the scan expert system 120 constructs the scan plan supporting screen containing the positioning image and the sectional image, and the constructed scan plan supporting screen is displayed on the display device 116, the operator operates the input device 115 to set the scan range of the full scan.

The operator operates the input device 115 so as to change the direction of the scan range auxiliary frame line superimposed on the positioning image illustrated in FIG. 9A1 (to swing the scan range auxiliary frame line), thereby changing the direction of the positioning image within the scan range auxiliary frame line to set the scan range of the full scan as illustrated in FIG. 9A2. As illustrated in FIG. 9A1, for example, when the positioning image is scanned with the subject obliquely inserted into the gantry 100, the operator operates the input device 115 to change the direction of the scan range auxiliary frame line, thereby straightening the direction of the subject within the scan range auxiliary frame line as illustrated in FIG. 9A2.

In other words, the operator changes the direction so that an area to be subjected to the full scan is contained within the scan range auxiliary frame line, thereby setting so that a desired area of the subject is scanned in the full scan. The following describes the details of the above processing with reference to FIGS. 9A1 and 9A2. FIGS. 9B1, 9B2 and 9B3 illustrate the details of the scan range setting in FIGS. 9A1 and 9A2. As illustrated in FIGS. 9A1 and 9A2, when the positioning image is scanned with the subject obliquely inserted into the gantry 100, a position relation between the subject S1 and the scan range auxiliary frame line is the position relation illustrated in FIG. 9B1. In other words, the subject S1 is oblique with respect to the scan range auxiliary frame line.

The operator then operates the input device 115 to swing the scan range auxiliary frame line in a direction of the arrow of (A) in FIG. 9B, thereby putting the desired area to be subjected to the full scan into the scan range auxiliary frame line as illustrated in (B) in FIG. 9B. This operation, as illustrated in (C) in FIG. 9B, causes an area containing the scan range auxiliary frame line in the subject S1 to be set as the scan range of the full scan. Thus, the operator swings the scan range auxiliary frame line in a certain direction, thereby enabling the scan range to be set so that the desired area is scanned in the full scan. The following describes pieces of processing of the respective units. When the input device 115 receives an operation to swing the scan range auxiliary frame line, for example, the scan expert system 120 supplies position information of the scan range auxiliary frame line after the swing to the projection image generation processing unit 122 and the three-dimensional image processing unit 121 based on information on the swing of the scan range auxiliary frame line received by the input device 115.

The projection image generation processing unit 122 generates a corresponding projection image within the scan range auxiliary frame line based on the position information of the scan range auxiliary frame line after the swing and supplies the projection image to the scan expert system 120. The three-dimensional image processing unit 121 generates a corresponding sectional image based on the position information of the scan range auxiliary frame line after the swing and supplies the sectional image to the scan expert system 120. The three-dimensional image processing unit 121, for example, generates an axial image at the scan starting position of the scan range auxiliary frame line after the swing and an axial image at the scan ending position of the scan range auxiliary frame line after the swing from the volume data and supplies the axial images to the scan expert system 120.

The scan expert system 120 constructs the scan plan supporting screen containing the projection image supplied from the projection image generation processing unit 122 and the sectional image supplied from the three-dimensional image processing unit 121 and causes the display device 116 to display the scan plan supporting screen. The scan expert system 120, for example, constructs the scan plan supporting screen illustrated in FIG. 9A2. The scan controller 110 sets the scan range of the full scan so as to contain the area within the scan range auxiliary frame line.

Next, a case of changing the projection direction in the entire projection image will be described. FIGS. 10A1, 10A2, 10B1, 10B2 and 10B3 are diagrams for illustrating an example of changing the projection direction in the entire projection image according to the present embodiment. FIGS. 10A1 and 10A2 illustrate an area of the scan plan supporting screen constructed by the scan expert system 120. As illustrated in FIGS. 10A1 and 10A2, for example, when the scan plan supporting screen constructed by the scan expert system 120 is displayed on the display device 116, the operator operates the input device 115 so as to change the direction of the positioning image illustrated in FIG. 10A1 (to swing the positioning image), thereby putting an area to be subjected to the full scan into the scan range auxiliary frame line to set the scan range of the full scan as illustrated in FIG. 10A2. As illustrated in FIG. 10A1, for example, when the positioning image is scanned with the subject obliquely inserted into the gantry 100, the operator operates the input device 115 to change the direction of the positioning image, thereby straightening the direction of the subject as illustrated in FIG. 10A2.

In other words, the operator changes the direction of the positioning image so that the area to be subjected to the full scan is contained within the scan range auxiliary frame line, thereby setting so that a desired area of the subject is scanned in the full scan. The following describes the details of the above processing with reference to FIGS. 10B1, 10B2 and 10B3. FIGS. 10B1, 10B2 and 10B3 illustrate the details of the scan range setting in FIGS. 10A1 and 10A2. As illustrated in FIGS. 10A1 and 10A2, when the positioning image is scanned with the subject obliquely inserted into the gantry 100, a position relation between the subject S1 and the scan range auxiliary frame line is the position relation illustrated in FIG. 10B1.

The operator then operates the input device 115 to swing the scan range auxiliary frame line in a direction of the arrow of FIG. 10B1, thereby putting the desired area to be subjected to the full scan into the scan range auxiliary frame line as illustrated in FIG. 10B2. This operation sets the area put into the scan range auxiliary frame line as the scan range. As illustrated in FIG. 10B3, the scan range setting is performed by changing the direction of the scan range auxiliary frame line with respect to the subject S1 by the amount of the change in the direction of the positioning image by the swing. In other words, the scan range auxiliary frame line is swung in the opposite direction by the amount of the swing of the positioning image, thereby setting an area containing the scan range auxiliary frame line in the subject S1 as the scan range of the full scan. Thus, the operator swings the positioning image in a certain direction, thereby enabling the scan range to be set so that the desired area is scanned in the full scan.

The following describes pieces of processing of the respective units. When the input device 115 receives an operation to swing the positioning image, for example, the scan expert system 120 supplies position information of the positioning image after the swing to the projection image generation processing unit 122 and the three-dimensional image processing unit 121 based on information on the swing of the positioning image received by the input device 115.

The projection image generation processing unit 122 generates a corresponding projection image based on the position information of the positioning image after the swing and supplies the projection image to the scan expert system 120. The three-dimensional image processing unit 121 generates a sectional image corresponding to the position of the scan range auxiliary frame line after the swing of the positioning image and supplies the sectional image to the scan expert system 120. The three-dimensional image processing unit 121, for example, generates an axial image corresponding to the scan starting position of the scan range auxiliary frame line and an axial image corresponding to the scan ending position of the scan range auxiliary frame line in the positioning image after the swing of the positioning image and supplies the axial images to the scan expert system 120.

The scan expert system 120 constructs the scan plan supporting screen containing the projection image supplied from the projection image generation processing unit 122 and the sectional image supplied from the three-dimensional image processing unit 121 and causes the display device 116 to display the scan plan supporting screen. The scan expert system 120, for example, constructs the scan plan supporting screen illustrated in FIG. 10A2. The scan controller 110 sets the scan range of the full scan so as to contain the area within the scan range auxiliary frame line.

Figure 11A:
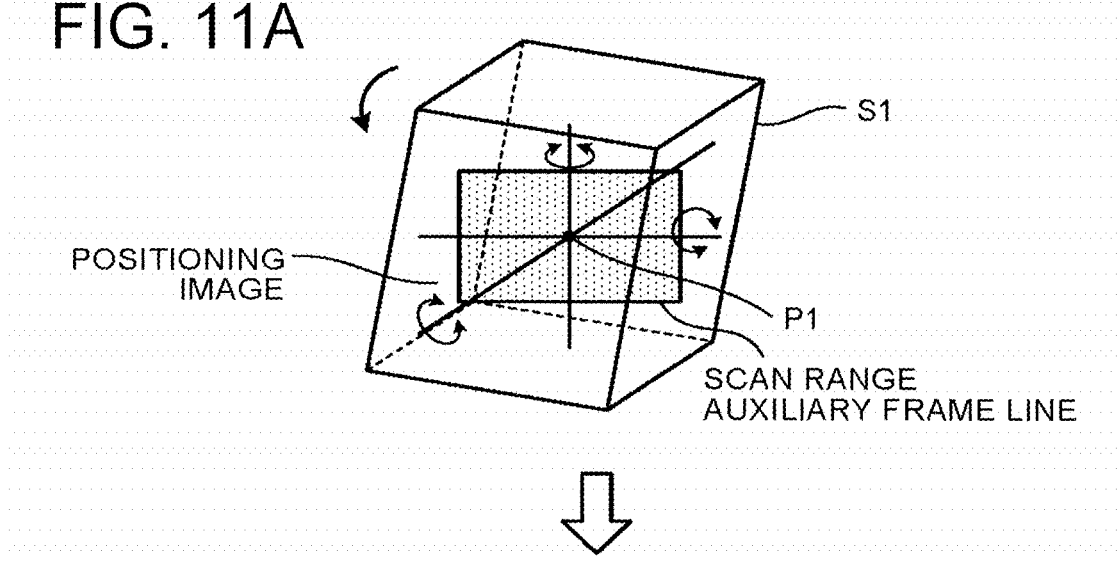
FIG. 11A is a diagram for illustrating a swing of a projection image and an auxiliary frame line according to the present embodiment.
Figure 11B:
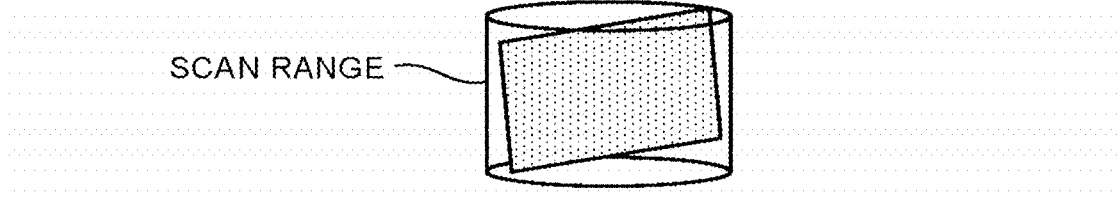
FIG. 11B is a diagram for illustrating a swing of a projection image and an auxiliary frame line according to the present embodiment.

As described above, the X-ray computer tomographic apparatus according to the present embodiment sets the scan range of the full scan through the swing of the projection image or the auxiliary frame line. The swing of the projection image or the auxiliary frame line according to the present embodiment is not limited to the above examples and may be performed in any direction. FIGS. 11A and 11B are diagrams for illustrating the swing of the projection image or the auxiliary frame line according to the present embodiment. As illustrated in FIG. 11A, for example, the swing of the projection image or the auxiliary frame line according to the present embodiment is to change the direction of the positioning image or the scan range auxiliary frame line with respect to the subject S1 to a certain direction. As an example, the swing is to rotate, with the point P1 in the positioning image or the scan range auxiliary frame line as the center, the projection image or the scan range auxiliary frame line with three axes orthogonal to each other at the point P1 as rotational axes.

In other words, the input device 115 receives the rotational operation illustrated in FIG. 11A, and as illustrated in FIG. 11B, the scan controller 110 sets an area contained in the scan range auxiliary frame line after the rotational operation on the positioning image or the scan range auxiliary frame line as the scan range of the full scan. The swing of the positioning image or the scan range auxiliary frame line may be performed after the size or position of the scan range of the full scan is changed or before the size or position of the scan range of the full scan is changed. In other words, the swing of the positioning image or the scan range auxiliary frame line and the changing of the size and the changing of the position of the scan range auxiliary frame line may be performed in combination appropriately.

The above embodiment describes a case of setting the area contained in the scan range auxiliary frame line after the rotational operation on the positioning image or the scan range auxiliary frame line as the scan range of the full scan. The scan expert system 120 can preset an angle after the rotational operation on the positioning image or the scan range auxiliary frame line as a projection direction of the positioning image. The scan expert system 120, for example, sets the angle after the rotational operation on the volume data as the projection direction of the positioning image. The scan expert system 120 constructs a preset button in the scan plan supporting screen. The scan expert system 120, for example, constructs the preset button as the positioning image direction selection button illustrated in FIG. 5. With this configuration, the user can easily reconstruct the angle set by the rotational operation.

Figure 12A:
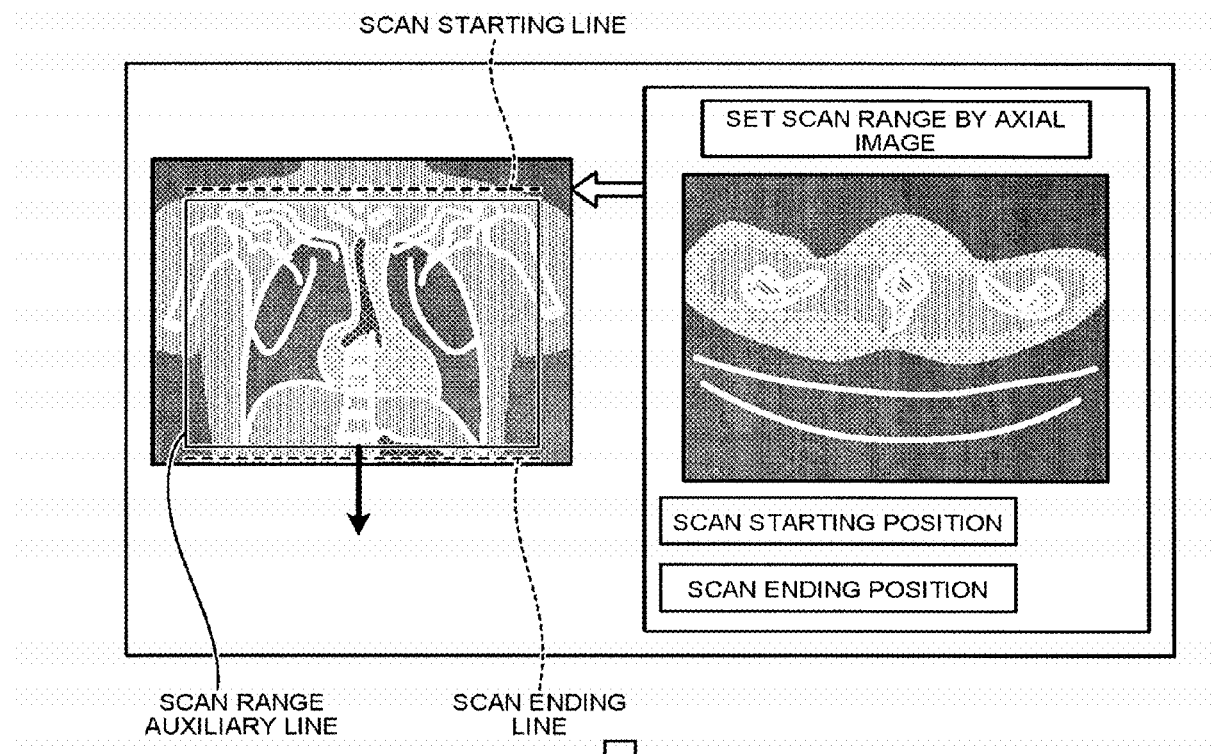
FIG. 12A is a diagram for illustrating an example of scan range setting according to the present embodiment.
Figure 12B:
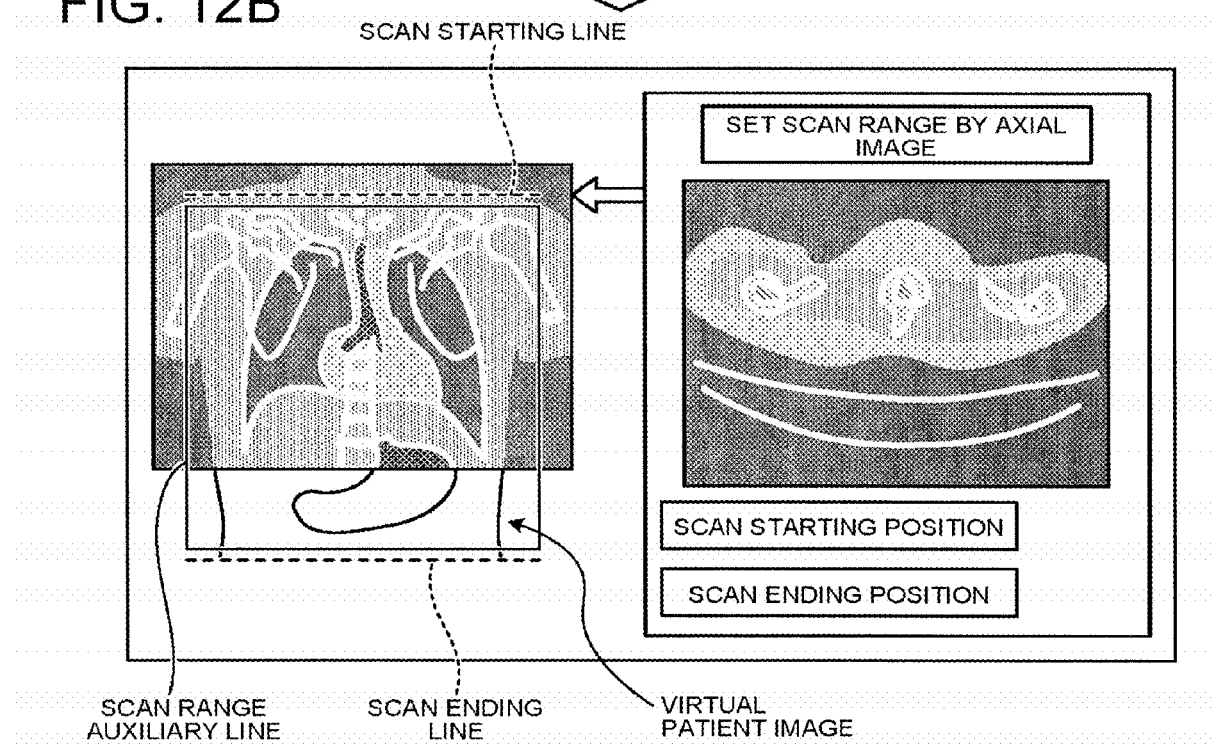
FIG. 12B is a diagram for illustrating an example of scan range setting according to the present embodiment.

The above embodiment describes a case of setting the scan range on the area contained in the projection image (positioning image). However, the X-ray computer tomographic apparatus according to the present embodiment can also set the scan range of the full scan on an area not scanned by the positioning scan. FIGS. 12A and 12B are diagrams for illustrating an example of scan range setting according to the present embodiment. FIGS. 12A and 12B illustrate an area of the scan plan supporting screen constructed by the scan expert system 120. As illustrated in FIG. 12A, for example, when the scan plan supporting screen constructed by the scan expert system 120 is displayed on the display device 116, the operator operates the input device 115 to enlarge the scan range auxiliary frame line, thereby setting the scan range of the full scan.

As illustrated in FIG. 12B, the X-ray computer tomographic apparatus according to the present embodiment enlarges the scan range auxiliary frame line to an area beyond the range of the positioning image, thereby setting the scan range of the full scan on the area not scanned by the positioning scan. Specifically, the scan controller 110, when the scan range of the second scan (full scan) is set on an unscanned area beyond the area of the projection image generated based on the projection data acquired through the first scan (positioning scan), performs control to acquire an area corresponding to the unscanned area in the subject from a virtual patient image corresponding to the unscanned area and to scan a scan range including the acquired area. In other words, the scan controller 110 acquires information on the area not scanned by the positioning scan from the virtual patient image prepared in advance to set the scan range.

The following describes the virtual patient image prepared in advance. The virtual patient images are a plurality of pieces of data corresponding to a plurality of respective combinations about parameters related to age, adult/child, male/female, physical constitutions such as height and weight, and the like and are stored in the storage device 112. The virtual patient images are prepared in advance as images actually X-ray photographed for human bodies having standard physical constitutions corresponding to combinations of the corresponding parameters. The human body has many anatomical characteristic points that can be extracted relatively easily from images based on morphologic characteristics and the like by image processing such as pattern recognition. The position and arrangement of these many anatomical characteristic points are roughly determined in accordance with age, adult/child, male/female, physical constitutions such as height and weight. These many anatomical characteristic points are detected in advance for the respective virtual patient images, and pieces of position data are stored concomitantly with or in association with the pieces of data of the virtual patient images together with identification codes of the respective anatomical characteristic points.

The scan expert system 120 extracts items such as age, adult/child, male/female, height, and weight from subject information and selects one virtual patient image out of a plurality of virtual patient images stored in the storage device 112 in accordance with the extracted items. The scan controller 110 acquires information on the area not scanned by the positioning scan from the virtual patient image selected by the scan expert system 120 to set the scan range. Before setting the scan range, anatomical characteristic points in the positioning image and anatomical characteristic points in the virtual patient image are compared to each other to perform positioning between the images.

Specifically, the region extraction processing unit 123 first extracts a plurality of anatomical characteristic points from the positioning image through image processing such as pattern recognition based on morphological characteristics or the like. The region extraction processing unit 123 holds pieces of position data of the respective extracted anatomical characteristic points and the identification codes of the respective anatomical characteristic points in an internal storage unit. The region extraction processing unit 123, based on the identification codes, performs position comparison and association between the anatomical characteristic points of the positioning image and the anatomical characteristic points of the virtual patient image. Specifically, the region extraction processing unit 123 compares the identification codes of the anatomical characteristic points extracted from the positioning image with the anatomical characteristic points on the virtual patient image with which the same identification codes are associated. The following describes the comparison of the anatomical characteristic points.

Figure 13:
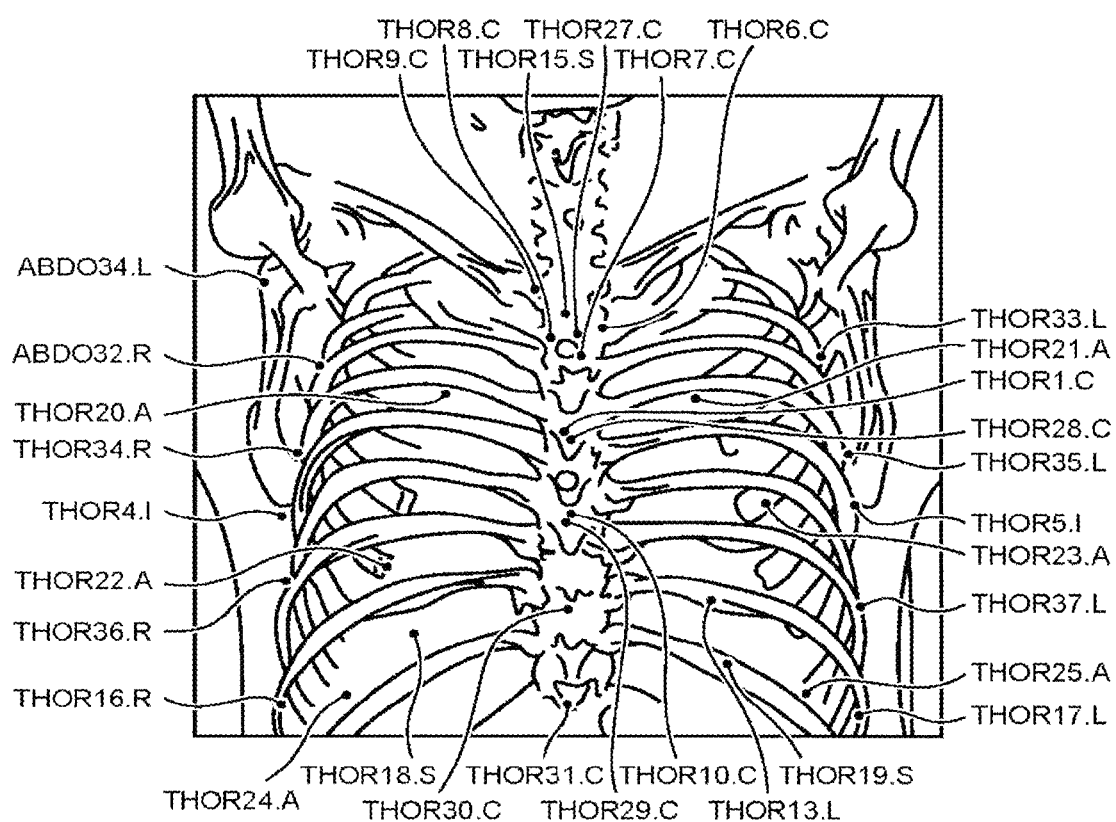
FIG. 13 is a diagram illustrating an example of anatomical characteristic points according to the present embodiment.

FIG. 13 is a diagram illustrating an example of anatomical characteristic points according to the present embodiment. As illustrated in FIG. 13, for example, the anatomical characteristic points are present on an image, in which anatomical characteristic identification codes (such as "ABDO34.L," and "ABDO32.R" in the diagram) are assigned to respective points. As described above, the anatomical characteristic point of the virtual patient image are detected in advance, to which the identification codes are given. When the positioning image is collected, the region extraction processing unit 123 extracts the anatomical characteristic points through image processing such as pattern recognition based on morphological characteristics or the like and gives the identification codes to the respective extracted anatomical characteristic points. The region extraction processing unit 123 compares the respective anatomical characteristic points in accordance with the identification codes of these anatomical characteristic points.

Figure 14:
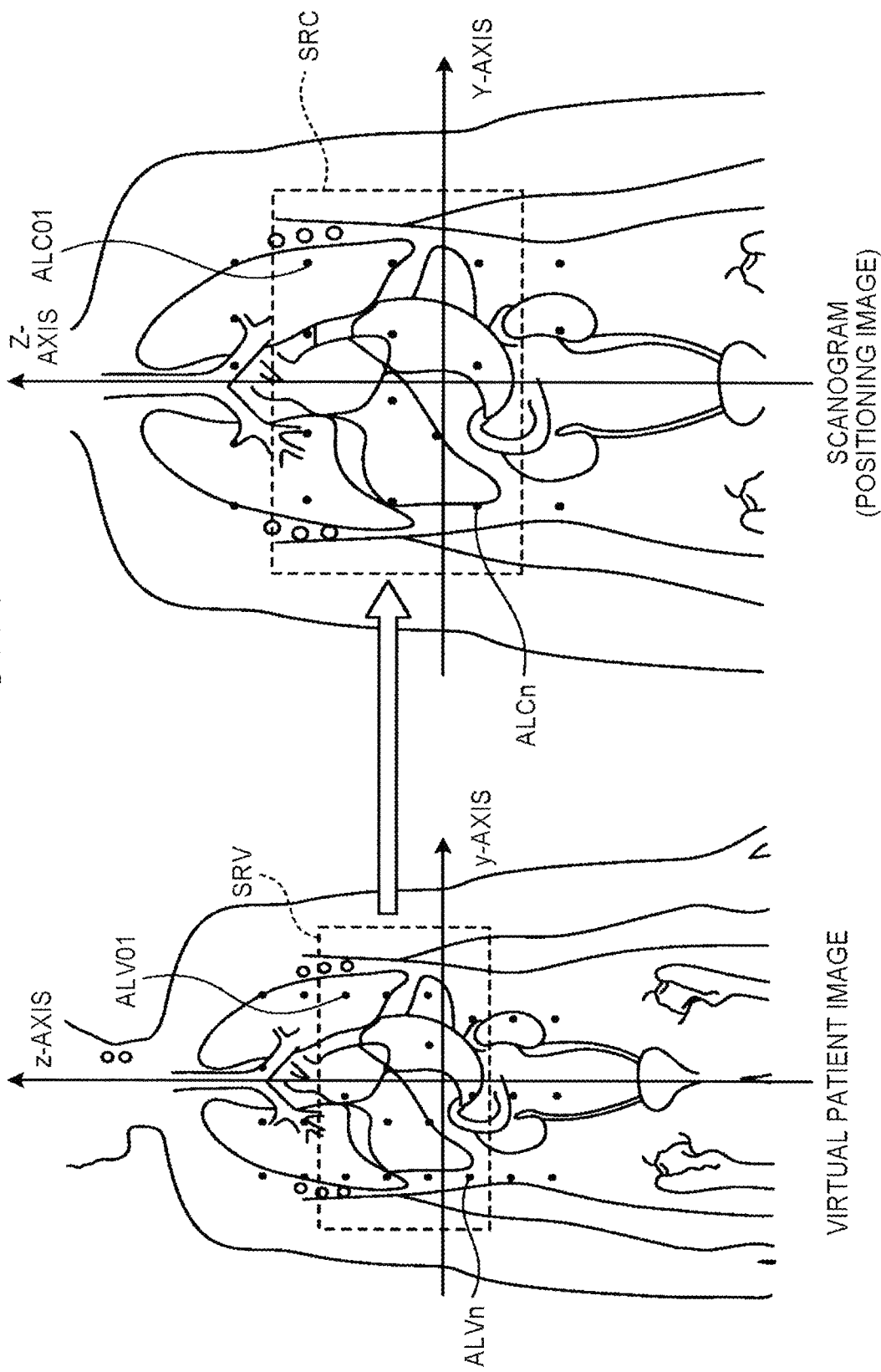
FIG. 14 is a diagram for illustrating an example of a comparison of anatomical characteristic points according to the present embodiment.

FIG. 14 is a diagram for illustrating an example of a comparison of anatomical characteristic points according to the present embodiment. As illustrated in FIG. 14, for example, the region extraction processing unit 123 compares a plurality of anatomical characteristic points ALV01 to ALVn on the virtual patient image with a plurality of anatomical characteristic points ALC01 to ALCn extracted from the positioning image. The same identification codes are associated with the anatomical characteristic points ALV01 to ALVn on the virtual patient image and the anatomical characteristic points ALC01 to ALCn extracted from the positioning image.

By thus performing the comparison between the anatomical characteristic points on the virtual patient image and the anatomical characteristic points on the positioning image, a scan range on the positioning image indicating the same anatomical range as a scan range set on the virtual patient image, for example, can be set. As an example, as illustrated in FIG. 14, the anatomical characteristic points ALV01 to ALVn contained in the scan range SRV designated on the virtual patient image are determined, and the scan range SRV is transformed into the scan range SRC so as to contain the anatomical characteristic points ALC01 to ALCn on the positioning image corresponding to the anatomical characteristic points ALV01 to ALVn.

In order to perform the scan range transformation, the region extraction processing unit 123 calculates a coordinate transform matrix for transforming between coordinates on the virtual patient image and coordinates on the positioning image. The region extraction processing unit 123, for example, calculates a coordinate transform matrix that transforms the coordinates on the virtual patient image into the coordinates on the positioning image (that is, coordinates in the scan space of the gantry 100). A coordinate transform matrix that transforms the coordinates on the positioning image into the coordinates on the virtual patient image may be calculated.

Figure 15:
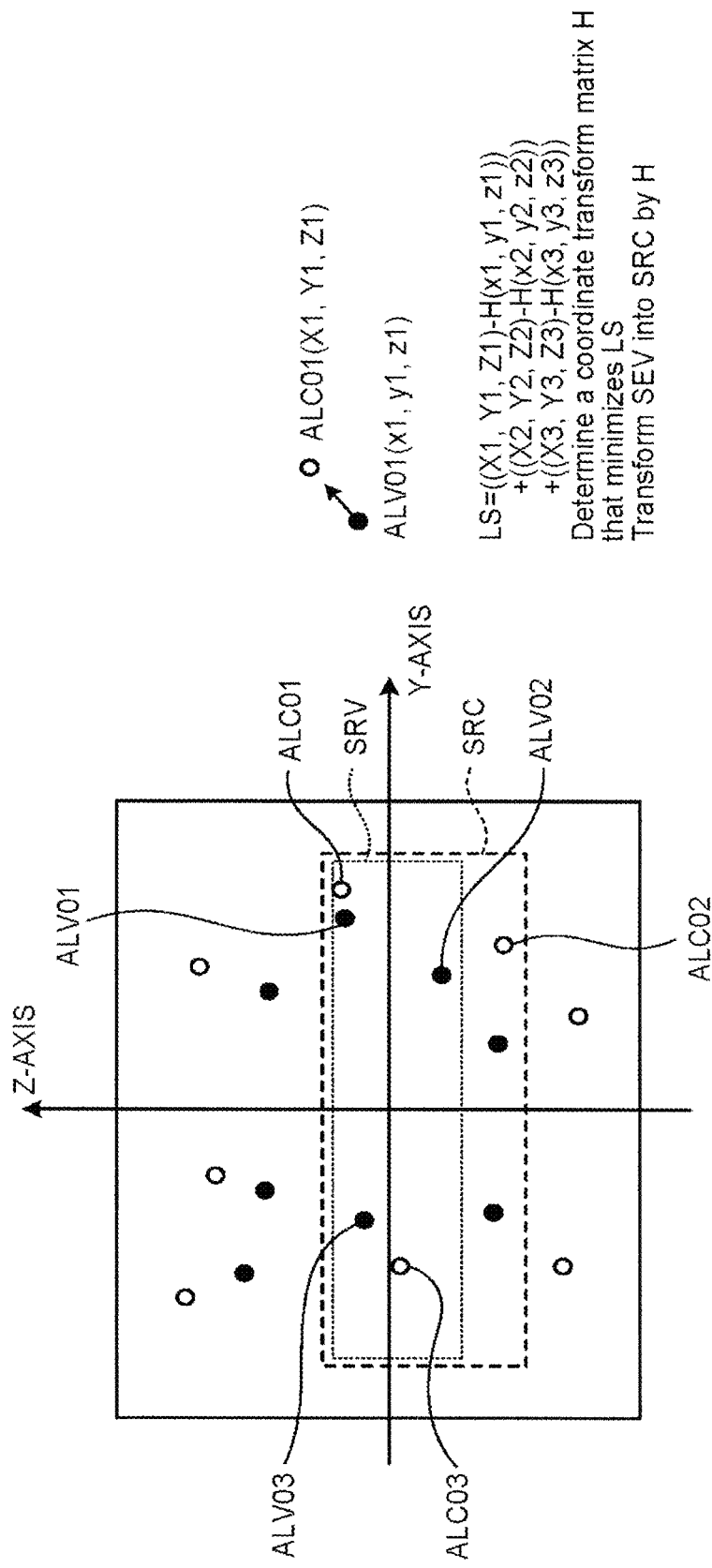
FIG. 15 is a diagram for illustrating an example of a coordinate transform matrix according to the present embodiment.

FIG. 15 is a diagram for illustrating an example of a coordinate transform matrix according to the present embodiment. FIG. 15 illustrates a case of transforming the scan area SRV set on the virtual patient image into the scan area SRC as a corresponding area on the positioning image. As illustrated in FIG. 15, for example, the region extraction processing unit 123 determines a coordinate transform matrix "H" so as to minimize a sum "LS" of deviations between the anatomical characteristic points that are anatomically the same between the virtual patient image and the positioning image (ALV01, ALC01), (ALV02, ALC02), and (ALV03, ALC03). In other words, the region extraction processing unit 123 calculates the coordinate transform matrix "H" so as to minimize "LS" in the equation below:

$$LS = ((X1,Y1,Z1) - H(x1,y1,z1)) + ((X2,Y2,Z2) - H(x2,y2,z2)) + ((X3,Y3,Z3) - H(x3,y3,z3))$$

The region extraction processing unit 123 calculates the coordinate transform matrix for each subject and supplies it to the scan controller 110. The scan controller 110 transforms the coordinates of the scan range set on the virtual image into the coordinates on the positioning image (the coordinates in the scan space of the gantry 100) using the coordinate transform matrix received from the region extraction processing unit 123 to set the scan range of the full scan. The scan expert system 120, when the scan range of the full scan is set on the unscanned area beyond the area of the projection image generated based on the projection data acquired through the positioning scan, displays the virtual patient image corresponding to the unscanned area in an area corresponding to the unscanned area in the scan range of the full scan.

As illustrated in FIG. 12B, for example, the scan expert system 120, when the scan range auxiliary frame line is set beyond the area of the positioning image on the scan planning screen, displays the virtual patient image on an area in which no data is acquired through the positioning scan. As the displayed virtual patient image, an image is used that contains a region contained in the positioning image or, when an adjacent region is estimated, the estimated region based on the anatomical characteristic points contained in the positioning image.

Thus, when the virtual patient image is displayed on the area not scanned in the positioning scan, and the scan range is set on the displayed virtual patient image, the scan controller 110 applies the coordinate transform matrix to the coordinates of the anatomical characteristic points contained in the virtual patient image to transform them into the coordinates on the positioning image (the coordinates in the scan space of the gantry 100) and sets the scan range of the full scan so as to contain the transformed coordinates.

Figure 16A:
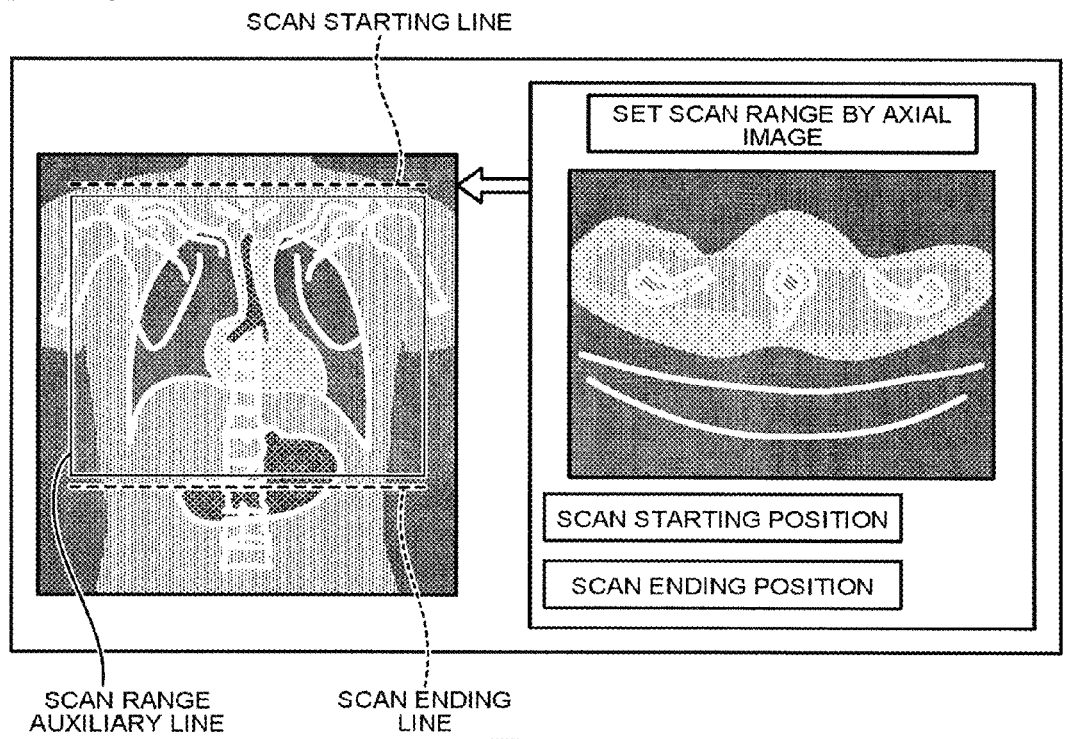
FIG. 16A is a diagram for illustrating an example of scan range setting according to the present embodiment.
Figure 16B:
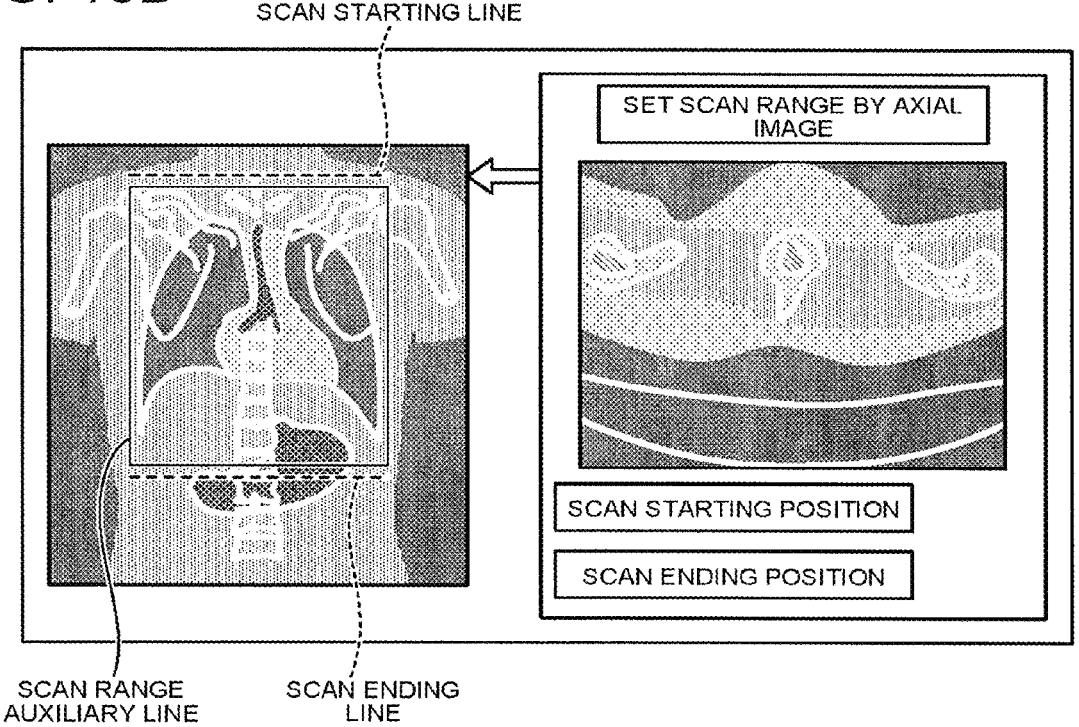
FIG. 16B is a diagram for illustrating an example of scan range setting according to the present embodiment.

Although the above example describes a case of changing the scan range auxiliary frame line with respect to the X-axial direction of the positioning image, embodiments are not so limited, and the scan range auxiliary frame line can be set in any direction. FIGS. 16A and 16B are diagrams for illustrating an example of scan range setting according to the present embodiment. FIGS. 16A and 16B illustrate an area of the scan plan supporting screen constructed by the scan expert system 120. As illustrated in FIG. 16A, for example, when the scan plan supporting screen constructed by the scan expert system 120 is displayed on the display device 116, the operator operates the input device 115 so as to change the width of the scan range auxiliary frame line in the Y-axial direction, thereby setting the scan range of the full scan as illustrated in FIG. 16B.

Thus, when the scan range in the Y-axial direction is changed by the operator, as illustrated in FIG. 16B, the scan expert system 120 changes an axial image to an axial image of the size after the change in the scan range. In other words, when the input device 115 receives the change in the scan range in the Y-axial direction, the scan expert system 120 sends information on the received range to the reconstruction processing unit 118. The reconstruction processing unit 118 reconstructs the volume data from the pieces of projection data collected through the positioning scan, with the sent range as the reconstruction range (D-FOV), and supplies the volume data to the three-dimensional image processing unit 121. The three-dimensional image processing unit 121 generates a sectional image corresponding to a desired position (the scan starting line or the scan ending line, for example) using the volume data supplied from the reconstruction processing unit 118 and supplies the sectional image to the scan expert system 120.

When the scan range in the Y-axial direction is changed by the operator, the scan controller 110 performs the full scan so as to contain the changed scan range. The scan controller 110 changes the size of C-FOV in accordance with the changed scan range. The scan controller 110, for example, controls the bow tie filter 131 or the collimator 132 in accordance with the change in the scan range in the Y-axial direction, thereby changing the size of C-FOV from "400 mm," which is the one at the time of the positioning scan, to "320 mm." This change can display the enlarged image with high resolution.

The embodiment when setting the scan range using the projection image generated based on the pieces of projection data collected through the positioning scan has been described. Next, the embodiment when setting the scan range using the sectional image generated based on the pieces of projection data collected through the positioning scan will be described. Although the following embodiment describes a case of using the axial image as the sectional image as an example, embodiments are not so limited, and the coronal image or the sagittal image may be used, for example.

In the X-ray computer tomographic apparatus of the present application when setting the scan range using the projection image, the scan expert system 120 designates a desired sectional image among sectional images generated based on the pieces of projection data through the first scan (positioning scan) and sets at least one end of the scan range of the second scan (full scan) based on the designated sectional image. Specifically, the input device 115 receives an operation on a display position of the sectional image generated based on the pieces of projection data acquired through the first scan. The scan expert system 120 sets at least one end of the scan range of the second range based on the sectional image the display position of which has been changed in accordance with the operation received by the input device 115.

In other words, the operator operates the input device 115 so as to perform the setting operation of the scan range on the sectional image, by which the scan expert system 120 sends the set information to the scan controller 110 and causes it to set the scan range. The input device 115 receives an operation for changing at least one of a sectional position and a sectional angle of the sectional image. The following describes scan range setting using the sectional image with reference to FIG. 17 and FIG. 18. FIG. 17 and FIG. 18 are diagrams for illustrating an example of scan range setting using the sectional image according to the present embodiment. FIG. 17 illustrates a case of setting the scan range by changing the sectional position of the sectional image. FIG. 18 illustrates a case of setting the scan range by changing the sectional angle of the sectional image. FIG. 17 and FIG. 18 each illustrate an area of the scan plan supporting screen constructed by the scan expert system 120.

Figure 17A:
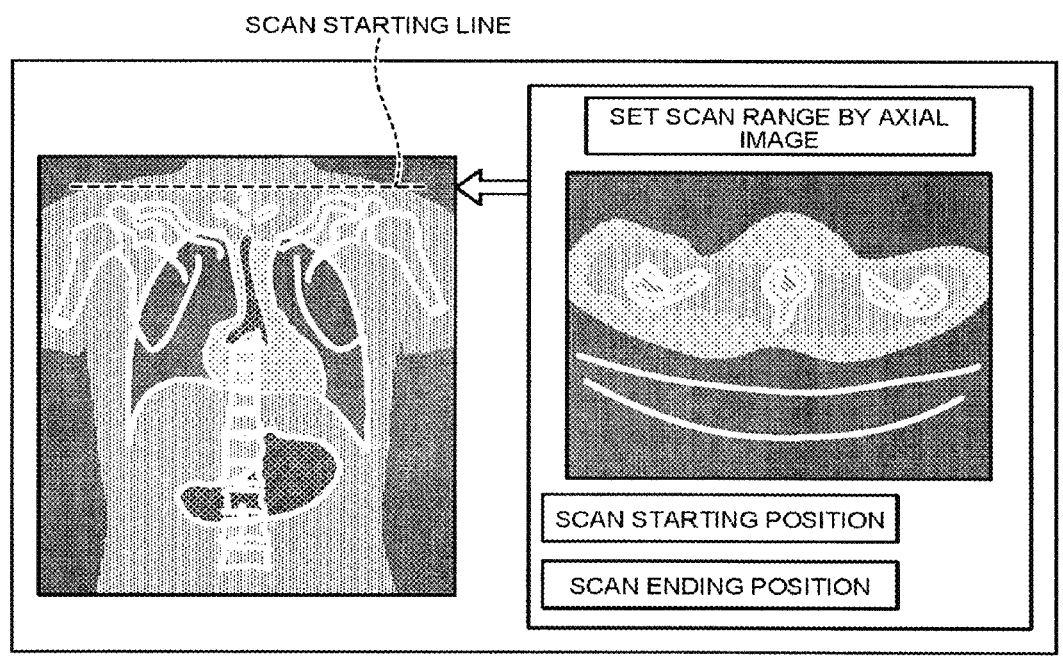
FIG. 17A is a diagram for illustrating an example of scan range setting using sectional images according to the present embodiment.
Figure 17B:
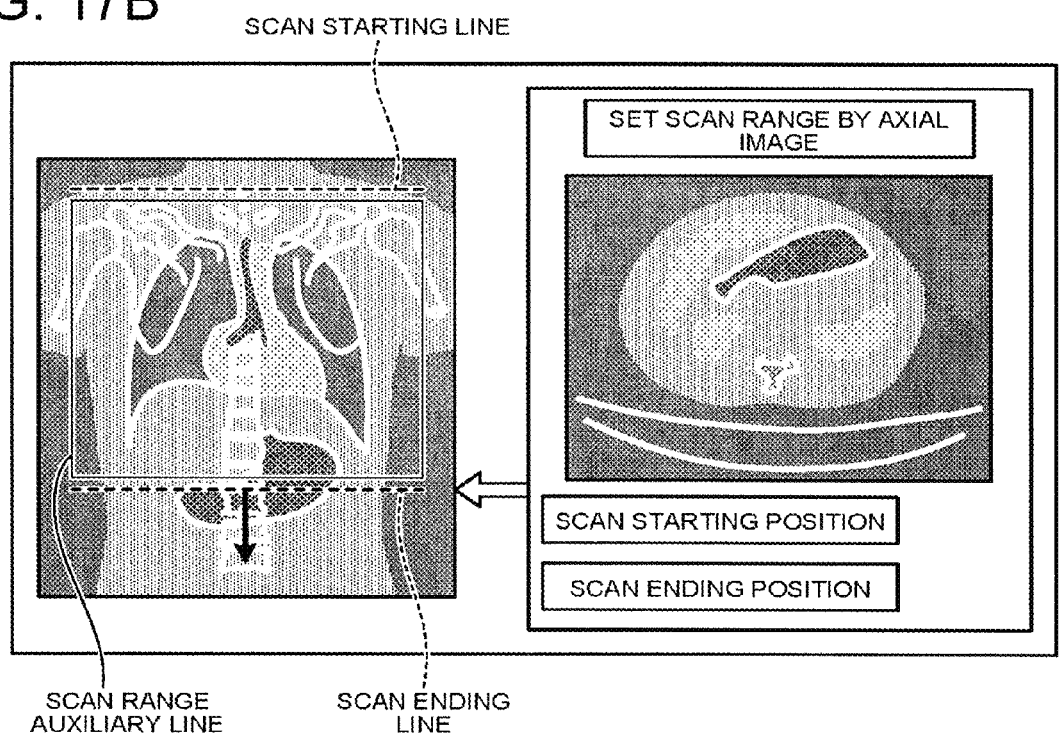
FIG. 17B is a diagram for illustrating an example of scan range setting using sectional images according to the present embodiment.
Figure 18A:
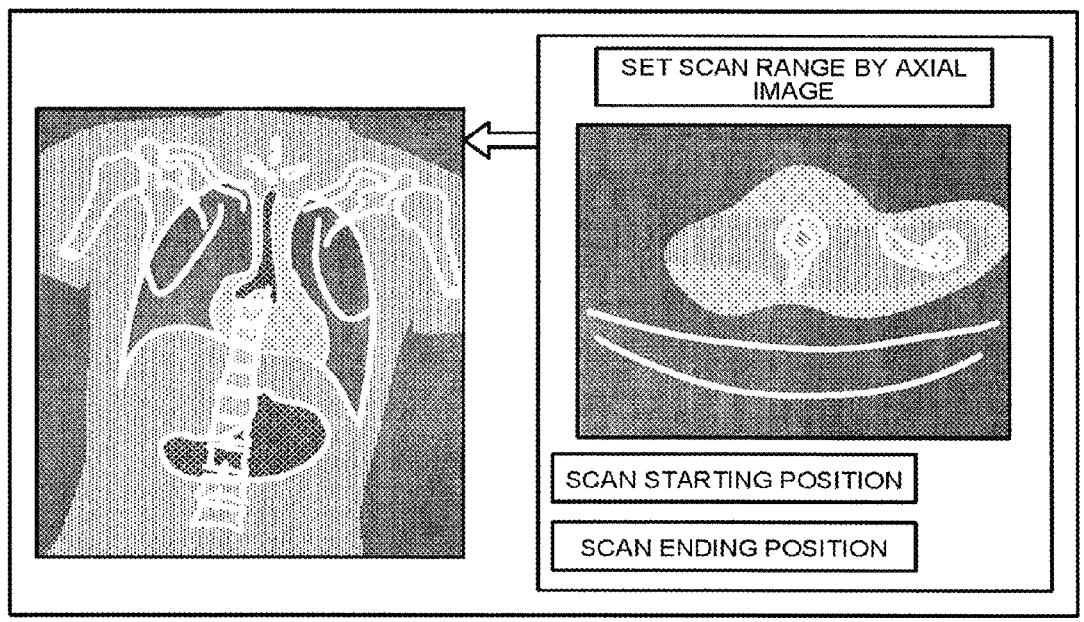
FIG. 18A is a diagram for illustrating an example of scan range setting using sectional images according to the present embodiment.
Figure 18B:
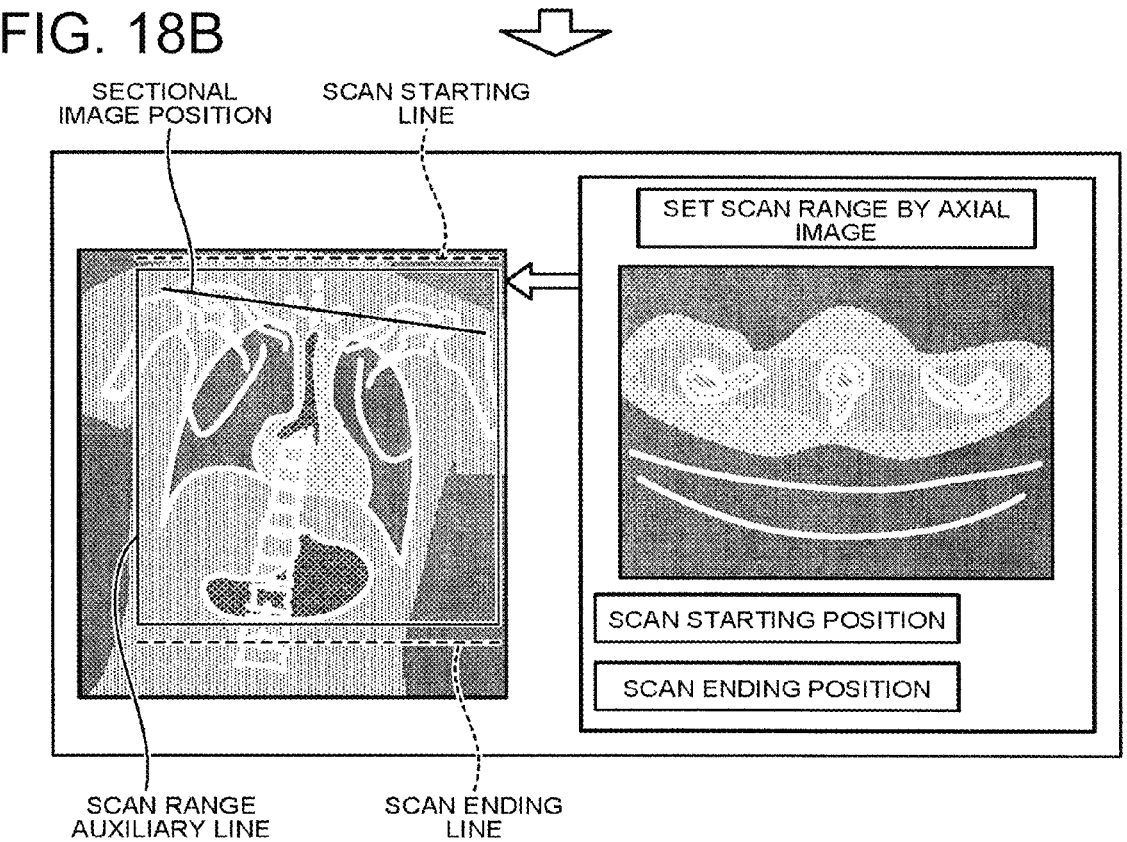
FIG. 18B is a diagram for illustrating an example of scan range setting using sectional images according to the present embodiment.

In other words, the operator operates the input device 115 so as to perform the setting operation of the scan range on the sectional image, by which the scan expert system 120 sends the set information to the scan controller 110 and causes it to set the scan range. The input device 115 receives an operation for changing at least one of a sectional position and a sectional angle of the sectional image. The following describes scan range setting using the sectional image with reference to FIGS. 17A, 17B, 18A and 18B. FIGS. 17A, 17B, 18A and 18B are diagrams for illustrating an example of scan range setting using the sectional image according to the present embodiment. FIGS. 17A and 17B illustrate a case of setting the scan range by changing the sectional position of the sectional image. FIGS. 18A and 18B illustrate a case of setting the scan range by changing the sectional angle of the sectional image. FIGS. 17A, 17B, 18A and 18B each illustrate an area of the scan plan supporting screen constructed by the scan expert system 120.

When the positioning image is collected through the positioning scan, for example, as illustrated in FIG. 17A, the scan expert system 120 constructs the scan planning screen containing the projection image (positioning image) generated by the pieces of projection data collected through the positioning scan and the axial image generated from the volume data reconstructed from the pieces of projection data. When the scan controller 110 causes the display device 116 to display the scan planning screen, the operator first presses the button "Set scan range by axial image" arranged on the screen. This operation can set the scan range by the axial image.

The operator operates the axial image via the input device 115 to set the scan range. The operator, for example, operates a mouse or the like on the axial image, thereby changing the sectional position of the axial image and presses the button "Scan starting position" at a desired position, thereby setting the sectional position of the sectional image when the button is pressed as a starting position of the scan range. The operator further changes the sectional position and presses the button "Scan ending position" at the sectional position illustrated in FIG. 17B, for example, thereby setting an ending position of the scan range. When the scan range is thus set via the input device 115, the scan expert system 120 sends the set information to the scan controller 110. The scan controller 110 sets the scan range of the full scan based on the sent information on the scan range and performs the full scan.

When the subject is obliquely inserted into the gantry 100 at the time of the positioning scan, and the positioning scan illustrated in FIG. 18A is displayed, for example, the operator first presses the button "Set scan range by axial image" in the same manner as the above to enable the scan range to be set by the axial image. The operator operates a mouse, a button, or the like on the axial image, thereby changing the sectional angle of the axial image and presses the button "Scan starting position" at a desired position, thereby setting the sectional position of the sectional image when the button is pressed as a starting position of the scan range. The operator, for example, operates the input device 115 to adjust the angle of the sectional image with respect to the X-Y plane or the X-Z plane, thereby changing the oblique axial image in FIG. 18A to the bisymmetric axial image in FIG. 18B. The operator presses the button "Scan starting position" to set a starting position of the scan range. The operator, after adjusting the angle, changes the sectional position of the axial image by operating a mouse or the like and presses the button "Scan ending position" in the same manner as the above, thereby setting an ending position of the scan range.

When the scan range is thus set via the input device 115, the scan expert system 120 sends the set information to the scan controller 110. The scan controller 110 sets the scan range of the full scan based on the sent information on the scan range and performs the full scan. As illustrated in FIG. 18B, when the sectional angle of the sectional image is changed, the scan expert system 120 can also display a line indicating a sectional image position at a position on the projection image (positioning image) corresponding to the axial image.

Although the above example describes a case where the operator changes the sectional angle of the sectional image as an example, the scan expert system 120 may automatically perform the change based on the anatomical characteristic points extracted by the region extraction processing unit 123. In such a case, the scan expert system 120 adjusts the sectional angle so that subject's regions contained in the axial image are bisymmetrically arranged based on the anatomical characteristic points extracted by the region extraction processing unit 123.

The scan range setting using the sectional image can also be set along with a change in a slice thickness. When the operator sets a desired slice thickness of "10.0 mm" while observing the axial image of the positioning scan performed with a slice thickness of "0.5 mm," for example, the scan controller 110 sets a range containing a marginal part for scanning an image of the slice thickness "10.0 mm" as the scan range. The scan expert system 120, for example, can also display the marginal part on the projection image (positioning image).

Figure 19:
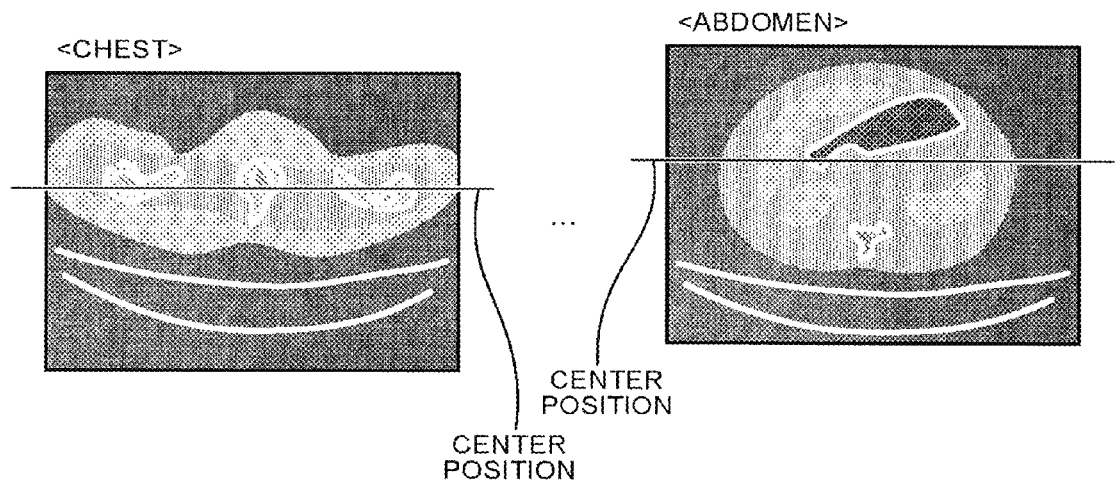
FIG. 19 is a diagram for illustrating an example of a change in a center position of each region according to the present embodiment.

A center of an image can also be set for each region while observing the axial image. FIG. 19 is a diagram for illustrating an example of a change in a center position for each region according to the present embodiment. As illustrated in FIG. 19, for example, the operator can set respective center positions of images for a chest and an abdomen while observing the axial image displayed on the scan planning screen. The chest and the abdomen, for example, have different distances from the top board to the center position of the body, and when the center position is determined in accordance with the chest, the center position of the abdomen may be on the upper part of the image. In view of this situation, the respective center positions of the images are set while changing the sectional position of the axial image. This operation enables the axial image displayed after the full scan to be displayed based on the set center position.

Figure 20:
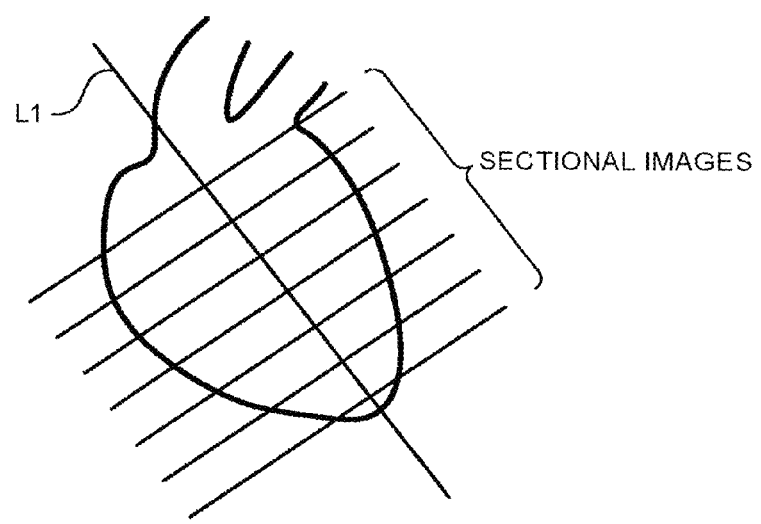
FIG. 20 is a diagram for illustrating scan range setting corresponding to sections of each region according to the present embodiment.

The present embodiment can also set the scan range by setting sections for each region. FIG. 20 is a diagram for illustrating scan range setting corresponding to sections of each region according to the present embodiment. As illustrated in FIG. 20, for example, sectional images orthogonal to the longitudinal axis L1 of a heart are often used for observing sections of the heart. The X-ray computer tomographic apparatus of the present application receives information on a desired section for each region and sets a range containing the received section as the scan range.

Specifically, the scan expert system 120 first displays the sectional image generated based on the pieces of projection data collected through the positioning scan on the scan planning screen. The input device 115 receives the operations of changing the position and angle of the sectional image and the scan starting position and the scan ending position and sends information on the received sectional image (coordinate information of the sectional image after changing the position and the angle, for example) to the scan expert system 120. The scan expert system 120 sends the information on the sectional image received from the input device 115 to the scan controller 110.

The scan controller 110 sets the scan range so as to contain the set sectional image based on coordinate information contained in the sectional image received from the scan expert system 120 and performs the full scan. The input device 115 can further narrow the scan range by receiving region information from the operator. In the above example, for example, the input device 115 receives region information "heart," by which the scan controller 110 sets a range containing the heart as the scan range. The inputting of the region information may be designated on the axial image or may be character input. In the case of character input, the scan controller 110 acquires the position (coordinates) of the heart based on the anatomical characteristic points extracted by the region extraction processing unit 123 and sets the scan range so as to contain the acquired position.

The scan controller 110, after performing the full scan, controls the scan expert system 120 so as to display the sectional image based on projection data collected through the full scan on a set section. When the scan range in the Y-axial direction is changed, the scan controller 110 changes the size of C-FOV by controlling the bow tie filter 131 or the collimator 132 in accordance with the changed scan range.

As described above, the X-ray computer tomographic apparatus according to the present embodiment can set the scan range using the projection image generated based on the projection data collected through the positioning scan or set the scan range using the sectional image generated based on the projection data collected through the positioning scan. Although the above embodiments are described as the examples separately embodied, embodiments are not so limited, and the scan range setting using the projection image and the scan range setting using the sectional image may be embodied in combination.

Specifically, the projection image and the sectional image contained in the scan planning screen constructed by the scan expert system 120 may be observed while moving them to set a desired scan range. As described above, the projection image and the sectional image on the scan planning screen constructed by the scan expert system 120 are linked together. When the projection image or the scan range auxiliary frame line is swung to set the scan starting position or the like, for example, the sectional image corresponding to it is displayed. When the angle or position of the sectional image is changed, information on the sectional image position is displayed at a corresponding position on the projection image.

Figure 21:
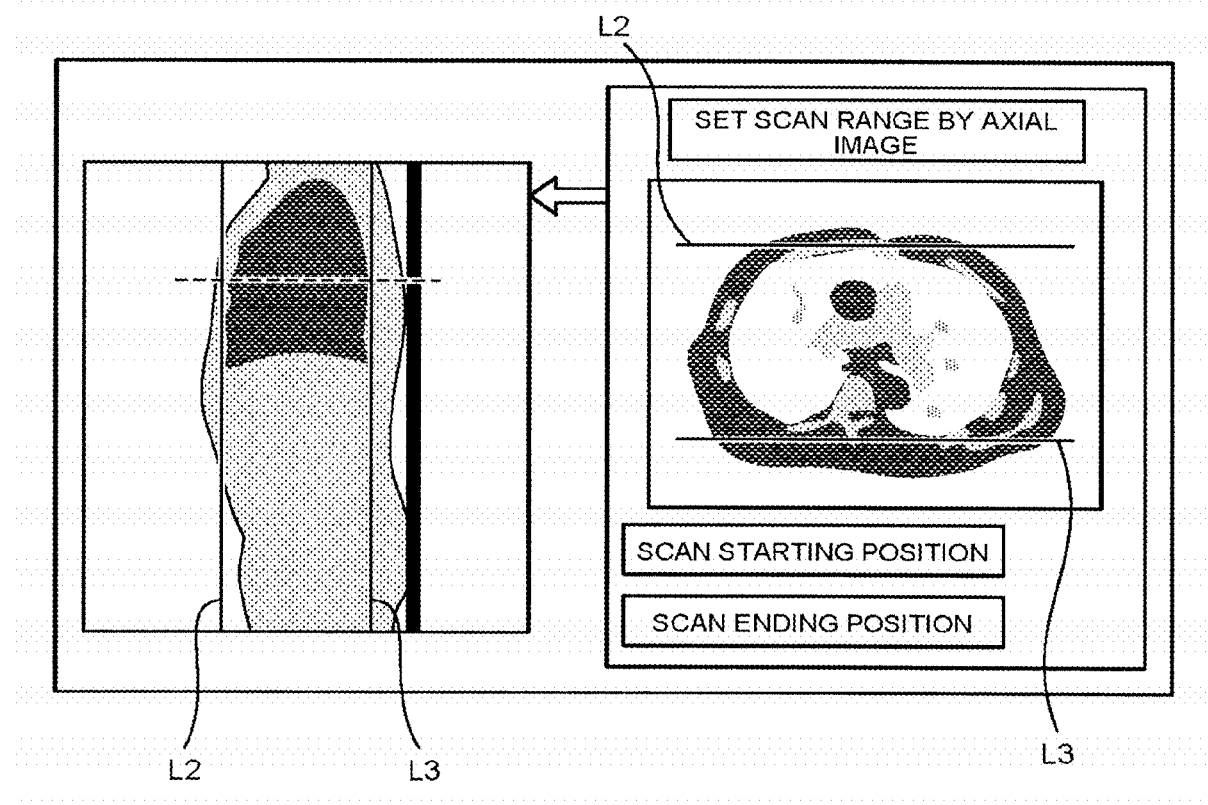
FIG. 21 is a diagram illustrating an example of a scan planning screen according to the present embodiment.

Thus, the operator can set the scan range while observing both the images and moving the images. The scan expert system 120 displays the projection image and the sectional image on different planes and displays the position of at least one end of the scan range of the second scan on the projection image and the sectional image in an associated manner. FIG. 21 illustrates an area of the scan planning screen constructed by the scan expert system 120. FIG. 21 illustrates an area of the scan plan supporting screen constructed by the scan expert system 120.

As illustrated in FIG. 21, for example, the scan expert system 120 displays the projection image and the sectional image on different planes. As illustrated in FIG. 21, the scan expert system 120 displays the lines L2 and L3 for setting the scan range at corresponding positions of both the images. The operator operates the input device 115 to move L2 and L3 displayed on the projection image or the sectional image, thereby setting the scan range. When the line L2 or the line L3 is moved in one image, the scan expert system 120 moves the corresponding line in the other image to a position corresponding to the movement.

The scan range can be thus set using the projection image and the sectional image, in which the displayed images are images of different planes. When one is the axial image, for example, the other is the coronal image or the sagittal image. When one is the coronal image, the other is the axial image or the sagittal image. When one is the sagittal image, the other is the axial image or the coronal image. Although the above embodiments describe a case of using the projection image and the sectional image, embodiments are not so limited, and a tomographic image and a tomographic image may be used.

Although the above embodiments describe a case of setting the scan range (the scan starting position and the scan ending position) as an example, only one end (the scan starting position or the scan ending position) may be set on the scan range. When the scan ending position is determined in advance, for example, only the scan starting position may be set. In contrast, when the scan starting position is determined in advance, only the scan ending position may be set.

It can also be set so that, for example, when only the scan starting position is set, the full scan is performed, the extraction of anatomical characteristic points by the region extraction processing unit 123 is performed in real time, and the full scan ends when the scan is performed up to a certain position.

Figure 22:
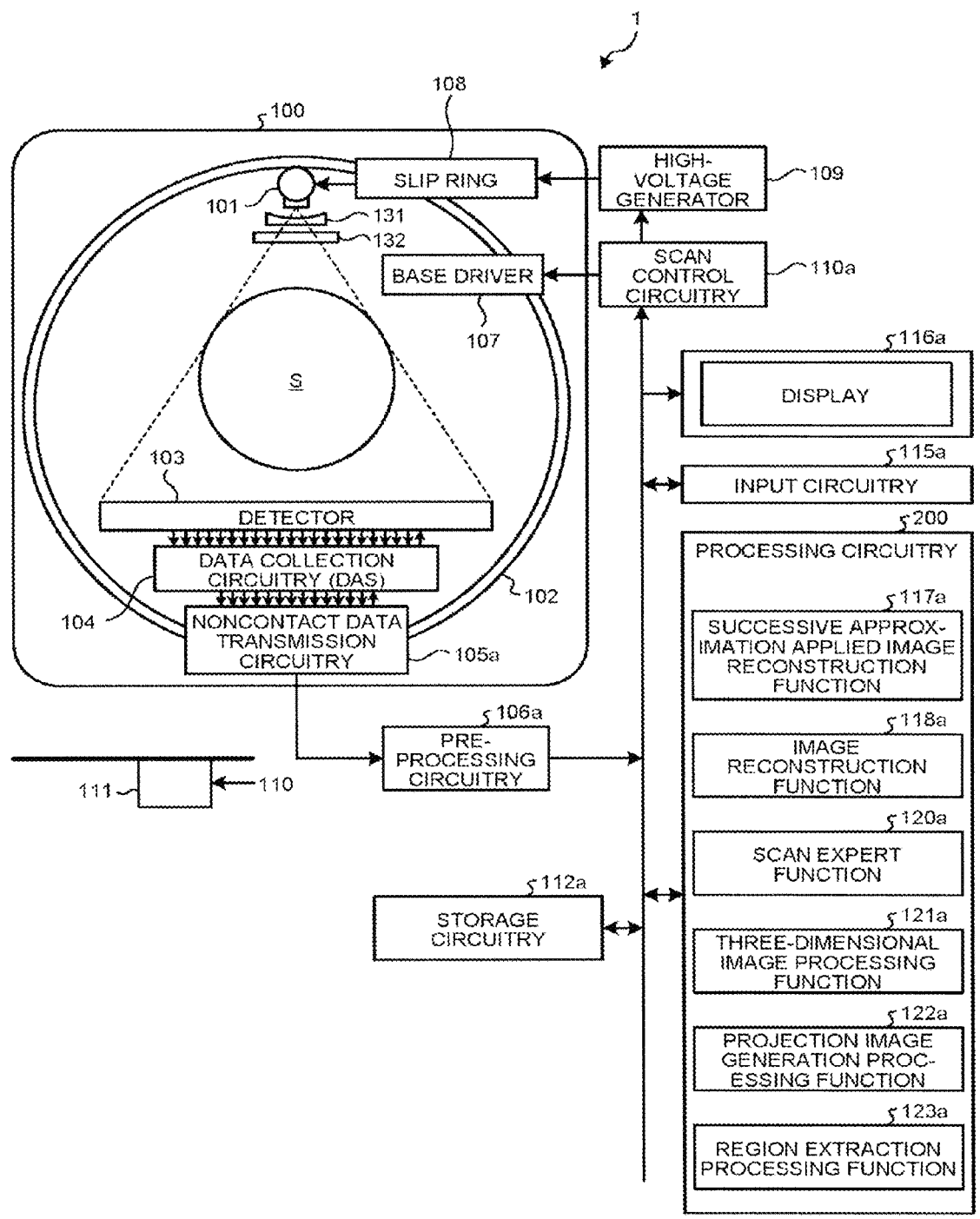
FIG. 22 is a diagram that illustrates an example of the configuration of an X-ray computer tomographic apparatus according to another embodiment.

Here, another embodiment of the X-ray computer tomographic apparatus described above will be described with reference to FIG. 22. FIG. 22 is a diagram that illustrates an example of the configuration of an X-ray computer tomographic apparatus 1 according to another embodiment. In another embodiment, the points different from the above embodiments are mainly explained, and as for functions similar to the components explained in the above embodiment, the same reference numerals are given thereto, and explanation thereof is omitted. As illustrated in FIG. 22, the X-ray computer tomographic apparatus 1 according to the other embodiment includes a gantry 100, preprocessing circuitry 106a, a high voltage generator 109, scan control circuitry 110a, storage circuitry 112a, a display 116a, input circuitry 115a and processing circuitry 200. As illustrated in FIG. 22, each circuitry is connected in each other and to transmit and receive various signals to each other. The preprocessing circuitry 106a corresponds to preprocessing device 106 illustrated in FIG. 1. The scan control circuitry 110a corresponds to the scan controller 110 illustrated in FIG. 1. The storage circuitry 112a corresponds to the storage device 112 illustrated in FIG. 1. The display 116a corresponds to the display device 116 illustrated in FIG. 1. The input circuitry 115a corresponds to the input device 115 illustrated in FIG. 1.

The gantry 100 includes an X-ray tube 101, a rotational frame 102, an X-ray detector 103, data collection circuitry 104, noncontact data transmission circuitry 105a, a base driver 107, a slip ring 108, a bow tie filter 131, and a collimator 132. In the embodiment in FIG. 22, the respective processing functions performed by the noncontact data transmission device 105, the pre-processing device 106, the scan controller 110, the successive approximation applied image reconstructing unit 117, the reconstruction processing unit 118, the scan expert system 120, the three-dimensional image processing unit 121, the projection image generation processing unit 122, and the region extraction processing unit 123 illustrated in FIG. 1 are stored in a storage circuitry 112a or a storage circuitry not illustrated, in the form of a computer-executable program. The noncontact data transmission circuitry 105a corresponds to the noncontact data transmission device 105 illustrated in FIG. 1.

Each of the data collection circuitry 104, the noncontact data transmission circuitry 105a, the preprocessing circuitry 106a, the scan control circuitry 110a and the processing circuitry 200 is a processor that loads programs from the storage circuitry 112a or a storage circuitry non-illustrated in FIG. 22, and executes the programs so as to implement the respective functions corresponding to the programs. In other words, each circuitry that has loaded the programs has the functions corresponding to the programs loaded. The term "processor" used in the above description means, for example, a central preprocess unit (CPU) and a graphics processing unit (GPU), or a circuit such as an application specific integrated circuit (ASIC), a programmable logic device (for example, a simple programmable logic device (SPLD)), a complex programmable logic device (CPLD), and a field programmable gate array (FPGA). The processor implements a function by loading and executing a program stored in a storage circuit. Instead of being stored in a storage circuit, the program may be built directly in a circuit of the processor. In this case, the processor implements a function by loading and executing the program built in the circuit. The processors in the present embodiment are not limited to a case in which each of the processors is configured as a single circuit. A plurality of separate circuits may be combined as one processor that implements the respective functions.

The storage circuitry 112a, for example, stores therein computer programs corresponding to a successive approximation applied image reconstruction function 117a, an image reconstruction function 118a, a scan expert function 120a, a three-dimensional image processing function 121a, a projection image generation processing function 122a, and a region extraction processing function 123a. The processing circuitry 200 reads the program corresponding to the successive approximation applied image reconstruction function 117a from the storage circuitry 112a and executes the program, thereby performing processing similar to the successive approximation applied image reconstructing unit 117. The processing circuitry 200 reads the program corresponding to the image reconstruction function 118a from the storage circuitry 112a and executes the program, thereby performing processing similar to the image reconstructing unit 118. The processing circuitry 200 reads the program corresponding to the scan expert function 120a from the storage circuitry 112a and executes the program, thereby performing processing similar to the scan expert system 120. The processing circuitry 200 reads the program corresponding to the three-dimensional image processing function 121a from the storage circuitry 112a and executes the program, thereby performing processing similar to the three-dimensional image processing unit 121. The processing circuitry 200 reads the program corresponding to the projection image generation processing function 122a from the storage circuitry 112a and executes the program, thereby performing processing similar to the projection image generation processing unit 122. The processing circuitry 200 reads the program corresponding to the region extraction processing function 123a from the storage circuitry 112a and executes the program, thereby performing processing similar to the region extraction processing unit 123.

The storage circuitry 112a, for example, stores therein computer programs corresponding to a scan control function to control the entire apparatus. The scan control circuitry 110a reads the program corresponding to the scan control function from the storage circuitry 112a and executes the program, thereby performing processing similar to the scan controller 110. The storage circuitry 112a or the storage circuitry non-illustrated, for example, stores therein computer programs corresponding to a data collection function, a noncontact data transmission function and a preprocessing function. The data collection circuitry 104, the noncontact data transmission circuitry 105a and the preprocessing circuitry 106a read the programs corresponding to the data collection function, the noncontact data transmission function and the preprocessing function from the storage circuitry 112a or the storage circuitry non-illustrated, and execute the program, thereby performing processing similar to The data collection circuitry 104, the noncontact data transmission device 105 and the preprocessing device 106.

The example illustrated in FIG. 22 describes a case of implementing the successive approximation applied image reconstruction function 117a, the image reconstruction function 118a, the scan expert function 120a, the three-dimensional image processing function 121a, the projection image generation processing function 122a, and the region extraction processing function 123a by causing one processing circuitry 200 to execute the respective programs. However, embodiments are not so limited, and for example, a plurality of processing circuits may implement the successive approximation applied image reconstruction function 117a, the image reconstruction function 118a, the scan expert function 120a, the three-dimensional image processing function 121a, the projection image generation processing function 122a, and the region extraction processing function 123a. For example, one or more functions among the successive approximation applied image reconstruction function 117a, the image reconstruction function 118a, the scan expert function 120a, the three-dimensional image processing function 121a, the projection image generation processing function 122a, and the region extraction processing function 123a may be separately implemented in exclusive, independent program execution circuits.

Some of the circuitry illustrated in FIG. 22 may be implemented as one processing circuit. For example, one program execution circuit may implement the scan control function implemented by the scan control circuitry 110a and the successive approximation applied image reconstruction function 117a, the image reconstruction function 118a, the scan expert function 120a, the three-dimensional image processing function 121a, the projection image generation processing function 122a, and the region extraction processing function 123a implemented by the processing circuitry 200.

The input circuitry 115a is implemented by a trackball, a switch button, a mouse, a keyboard, or the like for performing the setting of a scan position and a scan range or the like. The input circuitry 115a is connected to the scan control circuitry 110a, converts input operation received from an operator into an electric signal, and outputs the electric signal to the scan control circuitry 110a or the processing circuitry 200.

The following describes a processing procedure in the present embodiment with reference to FIG. 2. Step S11 in FIG. 2 is a step implemented by causing the scan control circuitry 110a to read the program corresponding to the scan control function from the storage circuitry 112a and to execute the program. At Step S11, the scan control circuitry 110a controls the base drive unit 107, the high-voltage generator 109, and the like, thereby performing data collection by the helical scan or the non-helical scan. Step S12 in FIG. 2 is a step implemented by causing the processing circuitry 200 to read the program corresponding to the successive approximation applied image reconstruction function 117a from the storage circuitry 112a and to execute the program. At Step S12, the processing circuitry 200 reconstructs volume data from the projection data stored in the storage circuitry 112a through the successive approximation applied reconstruction processing.

Step S13 in FIG. 2 is a step implemented by causing the processing circuitry 200 to read the program corresponding to the projection image generation processing function 122a from the storage circuitry 112a and to execute the program. At step S13, the processing circuitry 200 executes projection image generation processing from the projection data stored in the storage circuitry 112a. Step S16 in FIG. 2 is a step implemented by causing the processing circuitry 200 to read the program corresponding to the three-dimensional image processing function 121a from the storage circuitry 112a and to execute the program. At Step S16, the processing circuitry 200 performs the MPR processing on the volume data. At Steps S14 and S17, the display 116a displays a projection image and an MPR image, respectively, generated through the processing by the processing circuitry 200.

Step S15 and step S18 in FIG. 2 are steps implemented by causing the input circuitry 115a. At Steps S15 and S18, when the input circuitry 115a receives an operation related to the changing of the direction or the changing of the position of an image or the changing of the scan range auxiliary frame line from the operator, the input circuitry 115a converts the received operation into an electric signal and outputs the electric signal to the processing circuitry 200. When the processing circuitry 200 receives the electric signal from the input circuitry 115a, the processing circuitry 200 generates the projection image and the MPR image corresponding to the changing. The display 116a displays the generated projection image and MPR image. Thus, the operator performs the changing of the direction or position of the image or the changing of the scan range auxiliary frame line, thereby determining a scan position and range and a reconstruction position and range (Step S19) and determining a modulation direction and an optimum mA (Step S20).

Step S21 in FIG. 2 is a step implemented by causing the scan control circuitry 110a to read the program corresponding to the scan control function from the storage circuitry 112a and to execute the program. At Step S21, the scan control circuitry 110a controls the base drive unit 107, the high-voltage generator 109, and the like, thereby performing the full scan. Step S22 is a step implemented by causing the processing circuitry 200 to read the programs corresponding to the image reconstruction function 118a and the three-dimensional image processing function 121a from the storage circuitry 112a and to execute the programs. At Step S22, the processing circuitry 200 reconstructs volume data from the projection data collected by the full scan through the cone-beam reconstruction. Furthermore, the processing circuitry 200 generates display images such as the MPR image from the reconstructed volume data. The display 116a displays the generated display images. The above-described processing circuitry 200 is an example of a processing circuitry in the claims.

As described above, the embodiments can improve the accuracy and the convenience of planning the scan range or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computer tomographic apparatus comprising:
an X-ray tube;
a high-voltage generator configured to generate a tube voltage to be applied to the X-ray tube;
an X-ray detector configured to detect X-rays emitted by the X-ray tube and having passed through a subject;
a rotational frame configured to support the X-ray tube rotatably around the subject; and
processing circuitry configured to
control the high-voltage generator and the rotational frame in order to perform first scan and second scan on the subject,
generate a projection image and a sectional image based on projection data generated from output of the X-ray detector, and
when at least one end of a scan range of the second scan is set on part of a projection image generated based on projection data acquired through the first scan, display a sectional image corresponding to at least one end of the scan range among sectional images generated based on the projection data acquired through the first scan.

2. The X-ray computer tomographic apparatus according to claim 1, further comprising input circuitry configured to receive an operation on display of the projection image generated based on the projection data acquired through the first scan, wherein
the processing circuitry is configured to display a projection image corresponding to the operation received by the input circuitry, and
control to scan an area contained in the scan range of the second scan in the projection image displayed.

3. The X-ray computer tomographic apparatus according to claim 2, wherein
the input circuitry is configured to receive an operation to change a projection direction in the entire projection image or a projection direction in the scan range of the second scan set on the projection image.

4. The X-ray computer tomographic apparatus according to claim 1, wherein
the processing circuitry is configured to, when the scan range of the second scan is set on an unscanned area beyond the area of the projection image generated based on the projection data acquired through the first scan, control to acquire an area corresponding to the unscanned area in the subject from a virtual patient image corresponding to the unscanned area and to scan a scan range including the acquired area.

5. The X-ray computer tomographic apparatus according to claim 4, wherein
the processing circuitry is configured to, when the scan range of the second scan is set on an unscanned area beyond the area of the projection image based on the projection data acquired through the first scan, display the virtual patient image corresponding to the unscanned area in an area corresponding to the unscanned area in the scan range of the second scan.

6. The X-ray computer tomographic apparatus according to claim 1, wherein
the processing circuitry is configured to, when the scan range of the second scan is set, control at least one of a bow tie filter and a collimator so that the X-rays are applied to an area corresponding to the set scan range.

7. The X-ray computer tomographic apparatus according to claim 1, wherein
the processing circuitry is configured to display the projection image and the sectional image on different planes and display a position of at least one end of the scan range of the second scan on the projection image and the sectional image in an associated manner.

8. An X-ray computer tomographic apparatus comprising:
an X-ray tube;
a high-voltage generator configured to generate a tube voltage to be applied to the X-ray tube;
an X-ray detector configured to detect X-rays emitted by the X-ray tube and having passed through a subject;
a rotational frame configured to support the X-ray tube rotatably around the subject; and
processing circuitry is configured to
control the high-voltage generator and the rotational frame in order to perform first scan and second scan on the subject,
generate a projection image and a sectional image based on projection data generated from output of the X-ray detector, and
designate a desired sectional image among sectional images generated based on projection data acquired through the first scan and to set at least one end of a scan range of the second scan based on the designated sectional image.

9. The X-ray computer tomographic apparatus according to claim 8, further comprising input circuitry configured to receive an operation on a display position of the sectional image generated based on the projection data acquired through the first scan, wherein
the processing circuitry is configured to set at least one end of the scan range of the second scan based on the sectional image the display position of which has been changed in accordance with the operation received by the input circuitry.

10. The X-ray computer tomographic apparatus according to claim 9, wherein
the input circuitry is configured to receive an operation for changing at least one of a sectional position and a sectional angle of the sectional image.

11. The X-ray computer tomographic apparatus according to claim 8, wherein
the processing circuitry is configured to, when the scan range of the second scan is set, control at least one of a bow tie filter and a collimator so that the X-rays are applied to an area corresponding to the set scan range.

12. The X-ray computer tomographic apparatus according to claim 8, wherein
the processing circuitry is configured to display the projection image and the sectional image on different planes and display a position of at least one end of the scan range of the second scan on the projection image and the sectional image in an associated manner.

13. The X-ray computer tomographic apparatus according to claim 1, wherein
the processing circuitry is configured to generate the sectional image using volume data reconstructed from the projection image through successive approximation reconstruction.

14. The X-ray computer tomographic apparatus according to claim 1, wherein
the first scan is performed before the second scan, and
in the first scan, the projection data across circumference of the subject is collected with X-rays having a lower radiation dose than that of the second scan while the X-ray tube and the X-ray detector are rotating.

15. The X-ray computer tomographic apparatus according to claim 1, wherein a direction of the projection image with respect to the subject is changed as required.

16. The X-ray computer tomographic apparatus according to claim 15, wherein
the processing circuitry is configured to display a scan planning screen containing operating buttons for selecting the direction of the projection image with respect to the subject out of a plurality of directions.

17. The X-ray computer tomographic apparatus according to claim 1, wherein
the processing circuitry is configured to cause a scan planning screen to selectively display a sectional image related to a scan starting position of the scan range and a sectional image related to a scan ending position of the scan range and cause the scan planning screen to display operating buttons for switching between display of the sectional image related to the scan starting position and display of the sectional image related to the scan ending position.

18. The X-ray computer tomographic apparatus according to claim 1, wherein
the processing circuitry is configured to cause a scan planning screen to display an auxiliary line indicating a scan starting position of the scan range in a different display manner from an auxiliary line indicating a scan ending position.

19. A scan plan setting supporting apparatus comprising:
processing circuitry configured to
generate a projection image and a sectional image based on projection data generated from output of an X-ray detector and
when at least one end of a scan range of second scan is set on part of a projection image generated based on projection data acquired through first scan, display a sectional image corresponding to at least one end of the scan range among sectional images generated based on the projection data acquired through the first scan.

20. A scan plan setting supporting apparatus comprising:
processing circuitry configured to
generate a projection image and a sectional image based on projection data generated from output of an X-ray detector and
designate a desired sectional image among sectional images generated based on projection data acquired through first scan and to set at least one end of a scan range of second scan based on the designated sectional image.

* * * * *